(12) United States Patent
Pesci et al.

(10) Patent No.: US 7,442,798 B2
(45) Date of Patent: Oct. 28, 2008

(54) AUTOINDUCER MOLECULES AND USES THEREFOR

(75) Inventors: Everett C. Pesci, Greenville, NC (US); Barbara H. Iglewski, Fairport, NY (US); Jared B. J. Milbank, Ann Arbor, MI (US); James P. Pearson, Cambridge, MA (US); Andrew S. Kende, Pittsford, NY (US); Everett P. Greenberg, Iowa City, IA (US)

(73) Assignees: The University of Iowa Research Foundation, Iowa City, IA (US); University of Rochester, Rochester, NY (US); East Carolina University, Greenville, NC (US)

( * ) Notice: Subject to any disclaimer, the term of this patent is extended or adjusted under 35 U.S.C. 154(b) by 384 days.

(21) Appl. No.: 10/844,037

(22) Filed: May 11, 2004

(65) Prior Publication Data

US 2005/0009869 A1 Jan. 13, 2005

Related U.S. Application Data

(63) Continuation of application No. 09/945,325, filed on Aug. 31, 2001, now abandoned.

(60) Provisional application No. 60/229,715, filed on Aug. 31, 2000.

(51) Int. Cl.
*C07D 215/38* (2006.01)
(52) U.S. Cl. ........................ 546/157; 546/153
(58) Field of Classification Search ............... 546/153, 546/157
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,239,088 A | 8/1993 | Hoffman et al. | |
| 5,320,805 A | 6/1994 | Kramer et al. | |
| 5,536,750 A | 7/1996 | deSolms et al. | |
| 5,591,872 A | 1/1997 | Pearson et al. | |
| 5,593,827 A | 1/1997 | Bycroft et al. | |
| 5,686,472 A | 11/1997 | Anthony et al. | |
| 5,776,974 A | 7/1998 | Bycroft et al. | |
| 5,942,619 A | 8/1999 | Dekker et al. | |
| 6,337,347 B1 | 1/2002 | Livinghouse | |
| 6,455,031 B1 | 9/2002 | Davies et al. | |

FOREIGN PATENT DOCUMENTS

| | | |
|---|---|---|
| EP | 0 177 764 A1 | 5/1985 |
| JP | 58096079 | 6/1983 |
| JP | 59051267 | 3/1984 |
| JP | 60045568 | 3/1985 |
| JP | 07188208 | 7/1995 |
| JP | 11029307 | 2/1999 |
| JP | 11029430 | 2/1999 |
| JP | 2000-302682 | * 10/2000 |
| WO | WO 92/18614 A1 | 10/1992 |
| WO | WO 95/28929 A1 | 11/1995 |
| WO | WO 96/29392 A1 | 9/1996 |
| WO | WO 97/12868 A1 | 4/1997 |
| WO | WO 97/27851 A1 | 8/1997 |
| WO | WO 98/57618 A1 | 12/1998 |
| WO | WO 99/65889 A1 | 12/1999 |
| WO | WO 01/18248 | 3/2001 |

OTHER PUBLICATIONS

Bai, CA 143:231611, abstract only of Beijing Zhongyiyao Daxue Xuebao, 2000, 23(4), pp. 27-29.*
Bai, CA 132:342910, abstract only of Beijing Zhongyiyao Cax Xue, vol. 22(6), pp. 34-35, 1999.*
Zhou, CA 133:275839, Abstract of Beijing Zhong. Dax. Xue. vol. 23(2), pp. 21-22, 2000.*
Kim, CA 133:275963, abstract of Pharm & Tox, vol. 87(1), pp. 1-5, 2000.*
Rho, CA 132:21050, abstract only of Biol & PHarm Bull, VOl 22(10), pp. 1141-1143, 1999.*
Debitus, J Mar Biothechnol, vol. 6, pp. 136-141, 1998.*
Tang, CA 129:245022, abstract only of Yaozue Zuebao, vol. 33(2), pp. 121-127, 1998.*
Kim, CA 129:58714, abstract only of Planta Medica, vol. 64(5), pp. 490, 1998.*
Chuang, CA 121:141339, abstract only of Chinese Pharm J, vol. 46(1), pp. 89-97, 1994.*
Liu, CA 117:86638, abstract only of Yaoxue Xuebao, vol. 26(11), pp. 836-840, 1991.*
Wang, CA 117:167680, abstract only of Chem Res in Chinese Univ, vol. 7(2), pp. 124-128, 1991.*
Beifuss, CA 126:277634, abstract onf Synlett, (3), pp. 313-315, 1997.*
Meunier, CA 122:154931, abstract only of Biochem, vol. 34(3), pp. 1076-1083, 1995.*
Office Actions issued in U.S. Appl. No. 09/945,325 and dated Apr. 4, 2003; Nov. 17, 2003; and Feb. 18, 2004.

(Continued)

*Primary Examiner*—D. Margaret Seaman
(74) *Attorney, Agent, or Firm*—Lahive & Cockfield, LLP; Maria Laccotripe Zacharakis; A. Jacqueline Wizeman

(57) ABSTRACT

Novel bacterial quinolone signal molecules and, more particularly, *pseudomonas* quinolone signal ("PQS") molecules, e.g., 2-heptyl-3-hydroxy-4-quinolone, and analogs and derivatives thereof are described. Therapeutic compositions containing the molecules, and therapeutic methods, methods of for regulating gene expression, methods for identifying modulators of the autoinducer molecules, and methods of modulating quorum sensing signaling in bacteria using the compounds of the invention are also described.

18 Claims, 6 Drawing Sheets

OTHER PUBLICATIONS

Allison, D.G. et al., "A staining technique for attached bacteria and its correlation to extracellular carbohydrate production", *J. Microbiol. Methods*, 2:93-99 (1984).

Allison, D.G. et al., "The role of exopolysaccharides in adhesion of freshwater bacteria", *J. Gen. Microbiol.*, 133:1319-1327 (1987).

Ames, D.E. et al. "N-oxides of some hydroxy- and amino-quinolines," *Journal of the Chemical Society*, p. 3079-3082 (1956).

Anwar, H. et al., "Dynamic interactions of biofilms on mucoid *Pseudomonas aeruginosa* with tobramycin and piperacillin", *Antimicrob. Agents Chemother.*, 36:1208-1214 (1992).

Bainton, N.J. et al., "A general role for the *lux* autoinducer in bacterial cell signalling: Control of antibiotic synthesis in *Erwinia*", *Gene.*, 116:87-91 (1992).

Bainton, N.J. et al., "N-(3-oxohexaonyl)-L-homoserine lactone regulates carbepenem antibiotic production in *Erwinia carotovora*", *Biochem. J.*, 288:997-1004 (1992).

Bayer, V. et al. "Synthese de F-Alkyl-2 chromones et mise en evidence de leurs intermediaires reactionnels," *Journal of Fluorine Chemistry*, 20:497-505 (1982). [French with English abstract.]

Beck von Bodman, S. et al., "Capsular polysaccharide biosynthesis and pathogenicity in *Erwinia carotovora* require induction by an N-acylhomoserine lactone autoinducer", *J. Bacteriol.*, 177:5000-5008 (1995).

Beifuss et al. "A new two-step synthesis of quinolone alkaloids based on the regioselective addition of organometallic reagents to 4-silyloxyquinolinium triflates." *Synlett.* 3: 313-315 (1997).

Bever, et al., "Molecular Characterization and Nucleotide Sequence of the *Pseudomonas aeruginosa* Elastase Structural Gene," *Journal of Bacteriology*, 1988, vol. 170, No. 9, 4309-4314.

Boivin, J. et al., "Biodeterioration of Materials" In *Biodeterioration and biodegradation 8* (ed.) H.W. Rossmore, Elsevier Applied Science, London, pp. 53-62 (1991).

Bonini, B.F. et al. "Synthesis and properties of a new family of chiral mesogens containing the 2,3-dihydrobenzopyran nucleus," *J. Organ. Chem.*, 59:5930-5936 (1994).

Boyd, A. et al., "Sequence of the *algL* gene of *Pseudomonas aeruginosa* and purification of its alginate lyase product", *Gene*, 131:1-8 (1993).

Boyd, A. et al., "Role of alginate lyase in cell detachment of *Pseudomonas aeruginosa*", *Appl. Environ. Microbiol.*, 60:2355-2359 (1994).

Brint, J.M. et al., "Synthesis of mulitple exoproducts in *Pseudomonas aeruginosa* is under the control of RH1R-Rh1I. Another set of regulators in strain PAO1 with homology to the autoinducer-responsive LuxR-LuxI family", *J. Bacteriol.*, 177:7155-7163 (1995).

Budzikiewicz, H. et al. "Bakterieninhaltstoffe, V[1]: alkychinoline und deren N-Oxide aus *Pseudomonas aeruginosa*," *Monatshefte für Chemie*, 110:947-953 (1979). [German with English abstract.]

Cao, J-G. et al., "Purification and Structural Identification of an Autoinducer for the Luminescence System of *Vibrio harveyi*" *Journal of Biological Chemistry*, 1989, vol. 264, No. 36, pp. 21670-21676.

Cao, J-G. et al. ."Biosynthesis and Stereochemistry of the Autoinducer Controlling Luminescence in *Vibrio harveyi*," *Journal of Bacteriology*, 1993, vol. 175, No. 12, 3856-3862.

Chapon-Hervé, C. et al. "Regulation of the *xcp* secretion pathway by multiple quorum-sensing modulons in *Pseudomonas aeruginosa*", *Molecular Microbiology* 24(6):1169-78 (1997).

Choi, S.H. et al., "Genetic Dissection of DNA Binding and Luminescence Gene Activation by the *Vibrio fischeri* LuxR Protein," Journal of Bacteriology, 1992, vol. 174, No. 12, 4064-4069.

Christensen, B.E. et al., "Physical and chemical properties of biofilms", In: Characklis, W.G. et al (eds.) *Biofilms*. John Wiley & Sons, New York, pp. 93-130 (1990).

Cohen-Bazire, G. et al., "Kinetic studies of pigment synthesis by non-sulfur purple bacteria", *J. Cell. Comp. Physiol.*, 49:25-68 (1957).

Coppola, G.M. "The chemistry of 2H-3, 1-benzoxazine-2,4(1H)-dione (isatoic anhydride). 17[1]. Synthesis of 2-Alkyl-4-quinolone alkaloids via a one-step reaction on N-methylisatoic anhydride with methyl ketone enolates," *Journal of Heterocyclic Chemistry* 22(3):491-494 (1985).

Cornforth, J.W. et al. "Structure of a naturally occuring antagonist of dihydrostreptomycin", *The Biochemical Journal*, 63:124-130 (1956).

Costerton, J.W. et al., "Bacteriol biofilms in nature and disease", *Ann. Rev. Microbiol.*, 41:435-464 (1987).

Davies, D.G. et al., "Exopolysaccharide production in biofilms: Substratum activation of alginate gene expression by *Pseudomonas aeruginosa*", *Appl. Environ. Microbiol.*, 59:1181-1186 (1993).

Davies, D.G. et al., "Regulation of the alginate biosynthesis gene *algC* in *Pseudomonas aeroginosa* during biofilm development in continuous culture", *Appl. Environ. Microbiol.*, 61:860-867 (1995).

Debitus et al. "Quinolones from a bacterium and tyrosine metabolites from its host sponge, *Suberea creba* from the Coral Sea" *J Marine Biotechnol*. 6(3): 136-141 (1998).

DeKievit, T.R. et al., Quorum sensing, gene expression and *Pseudomonas* biofilms, *Methods in Enzymology* 310:117-128 (Sep. 1999).

Dempsey, M.J., "Marine bacterial fouling: A scanning electron microscope study", *Marine Biol.*, 61:305-315 (1981).

Eberhard, A. et al., "Structural identification of autoinducer of photobacterium fischeri luciferase", *Biochemistry*, 20:2444-2449 (1981).

Eberhard, A. et al., "Analogs of the autoinducer of bioluminescence in vibrio fischeri", *Arch. Microbiol.*, 146:35-40 (1986).

Eberhard, et al., "Synthesis of the *lux* gene autoinducer in *Vibrio fischeri* is positively autoregulated," *Archives of Microbiology*, 1991, vol. 155, 294-297.

EMBL accession No. AF004504 for *Pseudomonas aeruginosa* pyocyanine biosythesis operon, complete sequence (Jul. 4, 1997).

Finlay, B.B. et al., "Common themes in microbial pathogenicity", *Microbiol. Rev.*, 53:210-230 (1989).

Fletcher, M. "Adherence of marine micro-organisms to smooth surfaces", pp. 347-374. In Beachey, E.H. (ed.), *Bacterial Adherence* (receptors and recognition, series 3 vol. 6.) Chapman & Hall, London (1980).

Floodgate, G.D. "The mechanism of bacterial attachment to detritus in aquatic systems", *Memorie dell 'Istituto Italiano di idrobiologica Dott. Carco di Marchi* 29 (suppl.), 311-323 (1972).

Fuqua, W.C. et al. "Quorum sensing in bacteria: The luxR-luxI family of cell density-responsive transcriptional regulators", *J. Bacteriol.*, 176:269-275 (1994).

Gacesa, P., "Alginate-modifying-enzymes. A proposed unified mechanism of action for the lyases and epimerases", *FEBS Lett.*, 212:199-202 (1987).

Gambello, M.J. et al.,, "Cloning and Characterization of the *Pseudomonas aeruginosa lasR* Gene, a Transcriptional Activator of Elastase Expression," *Journal of Bacteriology*, 1991, vol. 173, No. 9, 3000-3009.

Gambello, M.J. et al., "LasR of *Pseudomonas aeruginosa* is a transcriptional activator of the alkaline protease gene (*apr*) and an enhancer of exotoxin A expression", *Infect. Immun.*, 61:1180-1184 (1993).

Geesey, G.G. et al., "Microscopic examination of natural sessile bacterial populations from an alpine stream", *Can. J. Microbiol.*, 23:1733-1736 (1997).

Givskov, M. et al., "Eukaryotic interference with homoserine lactone-mediated prokaryotic signalling", *J. Bacteriol.*, 178:6618-6622 (1996).

Goswami, A. et al., "Microbial Hydroxylation of Quadrone to 8a-Hydroxyquadrone," *Journal of Natural Products*, 1987, vol. 50, No. 1, 49-54.

Guilhon, G.M.S.P. et al., "2-alkyl-4-quinolone alkaloids and cinnamic acid derivatives from *Esenbeckia almawillia*" *Phytochemistry*, 37(4):1193-1195.

Hengge-Aronis, R., "Survival of hunger and stress: The role of *rpoS* in early stationary phase regulation in *E. coli*", *Cell*, 72:165-168 (1993).

Hirao, I. et al. "A convenient synthesis of 2- and 2,3-substituted 4H-chromen-4-ones," *Synthesis*, 22:1076-178.

Høiby, N. "*Pseudomonas aeruginosa* Infection in Cystic Fibrosis," *Acta. Path. Microbiol. Scand. Sect. B.*, 1974, vol. 82, 551-558.

Holloway, B.W., "Genetic recombination in *Pseudomonas aeruginosa*", J. Gen. Microbiol., 13:572-581 (1955).

Iglewski, B.H. et al., "NAD-Dependent Inhibition of Protein Synthesis by *Pseudomonas aeruginosa* Toxin," PNAS, 1975, vol. 72, 2284-2288.

Iglewski, B.H. et al., "*Pseudomonas aeruginosa* exoenzyme S: An adenosine diphosphate ribosyltransferase distinct from toxin A," *PNAS* 1978, vol. 75, No. 7, 3211-3215.

Jones, H.C. et al., "Electron microscopic study of a slime layer", *J. Bacteriol*, 99:316-325 (1969).

Jones, S. et al., "The *lux* autoinducer regulates the production of exoenzyme virulence in *Erwinia carotovora* and *Pseudomonas aeruginosa*," *EMBO Journal*, 1993, vol. 12, No. 6, 2477-2482.

Kaplan, H.B. et al., "Diffusion of autoinducer is involved in regulation of the *Vibrio fisheri* luminescence system", *J. Bacteriol.*, 163:1210-1214 (1985).

Kessler, E. et al., "Synthesis, Processing and Transport of *Pseudomonas aeruginosa* Elastase," *Journal of Bacteriology*, 1988, vol. 170, No. 11, 5241-5247.

Khoury, A.E. et al., "Prevention and control of bacterial infections associated with medical devices", *ASAIO J.*, 38:M174-M178 (1992).

Kintner, P.K. III, et al., "Carbohydrate interference and its correction in pectin analysis using the m-hydroxydiphenyl method", *J. Food Sci.*, 47:756-760 (1982).

Kostova, I. et al. "Alkaloids and coumarins from *Ruta graveolens*", *Monatshefte für Chemie*, 130(5):703-707 (1999).

Latifi, A. et al., "Multiple homologues of LuxR and LuxI control expression of virulence determinants and secondary metabolites through quorum sensing in *Pseudomonas aeruginosa* PAO1", *Mol. Microbiol.*, 17:333-343 (1995).

Latifi, A. et al., "A hierarchical quorum sensing cascade in *Pseudomonas aeruginosa* links the transcriptional activators lasR and RhlR (VsmR) to expression of the stationary-phase sigma factor RpoS", *Mol. Microbiol.*, 21:1137-1146 (1996).

Lee et al. "Determination of the alkaloids in coptis-evodia herb couple by capillary electrophoresis." *J Liq. Chrom. & Rel. Technol.* 20(1): 63-78 (1997).

Meighen, E.A. "Molecular Biology of Bacterial Bioluminescence," *Microbiological Reviews*, 1991, vol. 55, No. 1, 123-142.

Nicas, T.I. et al., "The contribution of exoproducts to virulence of *Pseudomonas aeruginosa*," *Canadian Journal of Microbiology*, 1985, vol. 31, No. 4, 387-392.

Nichols, W.W. et al., "The penetration of antibiotics into aggregates of mucoid and non-mucoid *Pseudomonas aeruginosa*", *J. Gen. Microbiol.*, 135:1291-1303 (1989).

Ochsner, U.A., et al., "Autoinducer-mediated regulation of rhamnolipid biosurfactant synthesis in *Pseudomonas aeruginosa*", *PNAS USA*, 92:6424-6428 (1995).

Passador, L. et al., "Expression of *Pseudomas aeruginosa* Virulence Genes Requires Cell-to-Cell Communication," *Science*, 1993, vol. 260, 1127-1129.

Passador, L. et al., "Functional analysis of the *Pseudomonas aeruginosa* autoinducer PAI"., *J. Bacteriology*, 1996, 5995-6000.

Pearson, J.P. et al., "Structure of the autoinducer required for expression of *Pseudomonas aeruginosa* virulence genes," *PNAS USA*, 1994, vol. 91, No. 1, 197-201.

Pearson, J.P. et al., "Roles of *Pseudomonas aeruginosa las* and *rhi* quorum-sensing systems in control of elastase and rhamnolipid biosynthesis genes" *Journal of Bacteriology* 179(18):5756-5767 (Sep. 1997).

Pesci, E.C. et al. "Regulation of *las* and *rhl* quorum sensing in *Pseudomonas aeruginosa*", *Journal of Bacteriology* 179(10):3127-32 (May 1997).

Pesci, E.C. et al. "Quinolone signaling in the cell-to-cell communication system of *Pseudomonas aeruginosa*," *Proc. Natl. Acad. Sci. USA*, 96:11229-11234 (1999).

Peterson, G.L., "A simplification of the protein assay method of Lowry et al. which is more generally applicable", *Anal. Biochem.*, 83:346-356 (1997).

Pierson, L.S. et al., "Phenazine antibiotic biosynthesis in *Pseudomonas aureofaciens* 30-84 is regulated by PhzR in response to cell density", *Journal of Bacteriology* 176(13):3966-74 (Jul. 1994).

Piper, K.R. et al., "Conjugation factor of *Agrobacterium tumefaciens* regulates Ti plasmid transfer by autoinduction," *Nature*, 1993, vol. 362, 448-450.

Pirhonen, et al., "A small diffusible signal molecule is responsible for the global control of virulence and exoenzyme production in the plant pathogen *Erwinia carotovora*," *EMBO Journal*, 1993, vol. 12, No. 6, 2467-2476.

Preiss, J. et al., "Alginic acid metabolism in bacteria. I. enzymatic formation of unsaturated oligosaccharides and 4-deoxy-L-*erythro*-5-hexoseulose uronic acid", *J. Biol. Chem.*, 237:309-316 (1962).

Ralling, G. et al., "Growth rate-dependent regulation of RNA polymerase synthesis in *Escherichia coli*," *Mol. Gen. Genet.*, 1985, vol. 201, 379-386.

Reimmann, C. et al., "The global activator GacA of *Pseudomonas aeruginosa* PAO positively controls the production of the autoinducer N-butyryl-homoserine lactone and the formation of the virulence factors pyocyanin, cyanide, and lipase", *Mol. Microbiol.* 1997 vol. 24 No. 2, 309-319.

Reynolds, H.Y. et al., "*Pseudomonas aeruginosa* Infections: Persisting Problems and Current Research to Find New Therapies," *Annals of Internal Medicine*, 1975, vol. 82, No. 6, 819-831.

Robson, N.D. et al., "Bacterial N-acyl-homoserine-lactone-dependent signalling and its potential biotechnological applications", *Trends in Biotechnol.* 1997, vol. 15, 458-464.

Somanthan, R. et al. "Synthesis of some 2-Alkyl-4-quinoline and 2-Alkyl-4methoxyquinoline alkaloids," *Journal of Heterocyclic Chemistry*, 18:1077-1079.

Schiller, N.L. et al., "Characterization of the *Pseudomonas aeruginosa* alginate lyase gene (*algL*): cloning, sequencing and expression in *Escherichia coli*", *J. Bacteriol.* 175:4780-4789 (19930).

Schripsema, J. et al., "Bacteriocin *small* of *Rhizobium leguminosarum* belongs to the class of *N*-acyl-L-homoserine Lactone molecules, known as autoinducers and as quorum sensing co-transcription factors", *J. Bacteriol.* 178:366-371 (1996).

Srinivasan, R. et al., "Biofilm parameters influencing biocide efficacy", *Biotech. Bioeng.* 46:553-560 (1995).

Stewart, G.S.A.B. et al., "Shedding New Light On Food Microbiology," *ASM News*, 1993, vol. 59, No. 5, 241-246.

Stewart, P.S., "Biofilm accumulation model that predicts antibiotic resistance of *Pseudomonas aeruginosa* biofilms", *Antimicrob. Agents Chemother.* 38:1052-1058 (1994).

Sutherland I.W. "Polysaccharides in the adhesion of marine and freshwater bacteria," pp. 329-338 in R.C. W. Berkeley, et al. (eds.), *Microbial Adhesion to Surfaces*. Ellis Horwood, London (1980).

Swift, S. et al., "A novel strategy for the isolation of *luxI* homologues: evidence for the widespread distribution of a LuxR:Lux1 superfamily in enteric bacteria", *Mol. Microbiol.* 10:511-520 (1993).

Takeda, R. Hakko Kogaku Zasshi 37: 59-63 (1959).

Tashiro, H. et al., "Penetration of biocides into biofilm", *Wat. Sci. Technol.* 23:1395-1403 (1991).

Throup, J. et al., "Characterization of the yenI/yenR locus from *Yersinia enterocolitica* mediating the synthesis of two N-acylhomoserine lactone signal molecules", *Mol. Microbio.*, 17:345-356 (1995).

Wallace, W.H. et al., "An *algD*-Bioluminescent reporter plasmid to monitor algiate production in biofilms", *Microb. Ecol.* 27:225-239 (1994).

Wardell, J.N. et al., "Microbes and surfaces" *Symposia for the Society for General Microbiology*. 34:351-378 (1983).

Wierenga and Skulnick, "General, Efficient, One-Step Synthesis of β-Keto Esters," *Journal of Organic Chemistry*, 1979, vol. 44, No. 2, 310-311.

Williams, P. et al., "Small molecule-mediated density-dependent control of gene expression in prokaryotes: Bioluminescence and the biosynthesis of carbapenem antibiotics," *FEMS Microbiology*, 1992, vol. 100, 161-167.

Winson, M.K. et al., "Multiple N-acyl-L-homoserine lactone signal molecules regulate production of virulence determinants and secondary metabolites in *Pseudomonas aeruginosa*", *Proc. Natl. Acad. Sci. USA*. 92:9427-9431 (1995).

Zhang, L. et al., "*Agrobacterium* conjugation and gene regulation by N-acyl-L-homoserine lactones", *Nature*. 362:446-448 (1993).

Zobell, C.E., "The effect of solid surfaces upon bacterial activity", *J. Bacteriol*. 46:39-56 (1943).

\* cited by examiner

AUTOINDUCER MOLECULES AND USES THEREFOR

RELATED APPLICATIONS

This application is a continuation of U.S. Utility patent application Ser. No. 09/945,325, filed on Aug. 31, 2001, now abandoned, which claims the benefit of U.S. Provisional Application No. 60/229,715, filed Aug. 31, 2000, the disclosures of which and the references cited therein are hereby incorporated herein by reference in their entireties. Related subject matter is disclosed in the following issued patent, published patent applications, and pending U.S. applications, the disclosures of which and the references cited therein are incorporated herein by reference in their entireties: U.S. Pat. No. 5,591,872, issued Jan. 7, 1997; U.S. Pat. No. 6,057,288, issued May 2, 2000; published international patent application WO 98/58075, published in English on Dec. 23, 1998; published international patent application WO 98/57618 A1, published in English on Dec. 23, 1998; published international patent application WO 99/65889, published in English on Dec. 23, 1999; and published international patent application WO 01/18248 A2, published in English on Mar. 15, 2001.

GOVERNMENT SUPPORT

This work was supported by National Institutes of Health Grant R01-AI33713 (to B.H.I. and A.S.K.), Cystic Fibrosis Foundation Research Fellowship Grants PESCI96FO and PESCI99I0(to E.C.P.), and National Institutes of Health Predoctoral Training Grant 5-T32AI07362 (to J.P.P.). E.P.G. was supported by grants from the Cystic Fibrosis Foundation (GREENB97ZO) and the National Science Foundation (MCB-9808308).

BACKGROUND OF THE INVENTION

Bacteria communicate with each other to coordinate expression of specific genes in a cell density dependent fashion. This "bacterial signaling" is a phenomenon called quorum sensing and response. Quorum sensing enables a bacterial species to sense its own number and regulate gene expression according to population density. In other words, quorum sensing is cell density-dependent regulation of genes that involves a freely diffusible molecule synthesized by the cell called an autoinducer (Fuqua, W. C. et al. (1996) *Annu. Rev. Microbiol.* 50:727-751; Salmond, G. P. C. et al. (1995) *Mol. Microbiol.* 16:615-624; Sitnikov, D. M. et al. (1995) *Mol. Microbiol.* 17:801-812). Autoinducers are described, e.g., in U.S. Pat. Nos. 5,591,872 and 5,593,827.

Autoinducer molecules and methods for the use of autoinducer molecules are described, for example, in U.S. Pat. Nos. 5,591,872 and 6,057,288, and in published PCT international patent application Nos. WO 98/57618, WO 98/58075, WO 99/65889, and WO 00/06177. Bacteria at a low cell density produce a basal level of autoinducer, and, as a population grows, autoinducer concentration increases concomitantly with cell density. On reaching a threshold concentration, autoinducer binds to and thereby activates an R protein, which then induces or ceases to repress specific target genes. In this manner, intercellular signals enable a bacterial population to control the expression of specific genes in response to cell density.

The paradigm system for quorum sensing is the lux system of the luminescent marine bacterium, *Vibrio fischeri*. *V. fischeri* exists at low cell densities in sea water and also at very high cell densities within the light organs of various marine organisms, such as the squid *Euprymna scolopes* (Pesci, E. C. et al. (1997) *Trends in Microbiol.* 5(4):132-135; Pesci, E. C. et al. (1997) *J. Bacteriol.* 179:3127-3132; Ruby, E. G. (1996) *Ann. Rev. Microbiol.* 50:591-624). At high cell densities, the *V. fischeri* genes encoding the enzymes required for light production are expressed. These genes are part of the lux ICDABEG operon and are regulated by the gene products of luxI and luxR (Baldwin, T. O. et al. (1989) *J. of Biolum. and Chemilum.* 4:326-341; Eberhard, A., et al. (1991) *Arch. of Microbiol.* 155:294-297; Gray, K. M. et al. (1992) *J. Bacteriol.* 174:4384-4390).

LuxI is an autoinducer synthase that catalyzes the formation of the *V. fischeri* autoinducer (VAI), N-(3-oxohexanoyl) homoserine lactone (Eberhard, A., et al. (1991) *Arch. of Microbiol.* 155:294-297; Seed, P. C. et al. (1995) *J. Bacteriol.* 177:654-659). The autoinducer freely diffuses across the cell membrane and at high cell densities, reaches a critical concentration (Kaplan, H. B. et al. (1985) *J. Bacteriol.* 163:1210-1214). At this critical concentration, VAI interacts with LuxR, a DNA-binding transcriptional regulator. The LuxR-VAI complex then binds to an upstream sequence of the lux operon called the "lux box", and activates transcription (Devine, J. H. et al. (1989) *PNAS* 86: 5688-5692; Hanzelka, B. A. et al. (1995) *J Bacteriol.* 177:815-817; Stevens, A. M. et al. (1994) *PNAS* 91:12619-12623). Since one of the genes of the operon is luxI, an autoregulatory loop is formed.

Many gram-negative bacteria have been shown to possess one or more quorum sensing systems (Fuqua, W. C. et al. (1996). *Annu. Rev. Microbiol.* 50:727-751; Salmond, G. P. C. et al. (1995) *Mol. Microbiol.* 16:615-624). These systems regulate a variety of physiological processes, including the activation of virulence genes. In addition, it has been recently demonstrated that quorum sensing is involved in biofilm formation (Davies, D. G. et al. (1998) *Science.* 280(5361):295-8).

The systems typically have acylated homoserine lactone ("HSL") ring autoinducers, in which the homoserine lactone ring is conserved. The acyl side chain, however, can vary in length and degree of substitution. *Pseudomonas aeruginosa* has two quorum sensing systems, las and rhl (Brint et al. 1995, Hanzelka et al. 1996, Baldwin et al., 1989, Passador et al. 1993, Pearson et al. 1997, Pesci et al. 1997). The two systems have distinct autoinducer synthases (lasI and rhlI), transcriptional regulators (lasR and rhlR), and autoinducers (N-(3-oxododecanoyl) homoserine lactone (HSL) and N-butyryl HSL) (Sitnikov et al., 1995, Stevens et al. 1994). N-(3-oxododecanoyl) homoserine lactone is synthesized by LasI along with a small amount of N-(3-oxooctanoyl) HSL and N-(3-oxohexanoyl) HSL, while RhlI makes primarily N-butyryl HSL and a small amount of N-hexanoyl (Pearson et al. 1994, Winson et al. 1995). The rhl and las systems are involved in regulating the expression of a number of secreted virulence factors, biofilm development, and the stationary phase sigma factor (RpoS) (Brint et al. 1995, Davies et al. 1998, Latifi et al. 1996, Ochsner et al. 1995, Pesci et al. 1997). Expression of the rhl system requires a functional las system. Therefore the two systems in combination with RpoS constitute a regulatory cascade (Pesci et al. 1997, Seed et al. 1995).

Biofilms are defined as an association of microorganisms, single or multiple species, that grow attached to a surface and produce a slime layer that provides a protective environment (Costerton, J. W. (1995) *J Ind Microbiol.* 15(3): 137-40, Costerton, J. W. et al. (1995) *Annu Rev Microbiol.* 49:711-45). Typically, biofilms produce large amounts of extracellular polysaccharides, responsible for the slimy appearance, and are characterized by an increased resistance to antibiotics (1000- to 1500-fold less susceptible). Several mechanisms are proposed to explain this biofilm resistance to antimicrobial agents (Costerton, J. W. et al. (1999) *Science.* 284(5418): 1318-22). One idea is that the extracellular matrix in which the bacterial cells are embedded provides a barrier toward penetration by the biocides. A further possibility is that a majority of the cells in a biofilm are in a slow-growing, nutrient-starved state, and therefore not as susceptible to the effects of antimicrobial agents. A third mechanism of resistance could be that the cells in a biofilm adopt a distinct and protected biofilm phenotype, e.g., by elevated expression of drug-efflux pumps.

In most natural settings, bacteria grow predominantly in biofilms. Biofilms of *P. aeruginosa* have been isolated from medical implants, such as indwelling urethral, venous or peritoneal catheters (Stickler, D. J. et al. (1998) *Appl Environ Microbiol.* 64(9):3486-90). Chronic *P. aeruginosa* infections in cystic fibrosis lungs are considered to be biofilms (Costerton, J. W. et al. (1999) *Science.* 284(5418): 1318-22).

In industrial settings, the formation of biofilms is often referred to as 'biofouling', or biological fouling. Biological fouling of surfaces is common and leads to material degradation, product contamination, mechanical blockage, and impedance of heat transfer in water-processing systems. Biofilms are also the primary cause of biological contamination of drinking water distribution systems, due to growth on filtration devices.

As noted earlier, many gram-negative bacteria have been shown to possess one or more quorum sensing systems that regulate a variety of physiological processes, including the activation of virulence genes and biofilm formation. One such gram negative bacterium is *Pseudomonas aeruginosa*.

*P. aeruginosa* is a soil and water bacterium that can infect animal hosts. Normally, the host defense system is adequate to prevent infection. However, in immunocompromised individuals (such as burn patients, patients with cystic fibrosis, or patients undergoing immunosuppressive therapy), *P. aeruginosa* is an opportunistic pathogen, and infection with *P. aeruginosa* can be fatal (Govan, J. R. et al. (1996) *Microbiol Rev.* 60(3):539-74; Van Delden, C. et al. (1998) *Emerg Infect Dis.* 4(4):551-60).

For example, Cystic fibrosis (CF), the most common inherited lethal disorder in Caucasian populations (~1 out of 2,500 life births), is characterized by bacterial colonization and chronic infections of the lungs. The most prominent bacterium in these infections is *P. aeruginosa*—by their mid-twenties, over 80% of people with CF have *P. aeruginosa* in their lungs (Govan, J. R. et al. (1996) *Microbiol Rev.* 60(3):539-74). Although these infections can be controlled for many years by antibiotics, ultimately they "progress to mucoidy," meaning that the *P. aeruginosa* forms a biofilm that is resistant to antibiotic treatment. At this point the prognosis is poor. The median survival age for people with CF is the late 20s, with *P. aeruginosa* being the leading cause of death (Govan, J. R. et al. (1996) *Microbiol Rev.* 60(3):539-74). According to the Cystic Fibrosis Foundation, treatment of CF cost more than $900 million in 1995 (Foundation, CF http://www.cff.org/homeline199701.htm).

*P. aeruginosa* is also one of several opportunistic pathogens that infect people with AIDS, and is the main cause of bacteremia (bacterial infection of the blood) and pneumonitis in these patients (Rolston, K. V. et al. (1990) *Cancer Detect Prev.* 14(3):377-81; Witt, D. J. et al. (1987) *Am J. Med.* 82(5):900-6). A recent study of 1635 AIDS patients admitted to a French hospital between 1991-1995 documented 41 cases of severe *P. aeruginosa* infection (Meynard, J. L. et al. (1999) *J Infect.* 38(3): 176-81). Seventeen of these had bacteremia, which was lethal in 8 cases. Similar numbers were obtained in a smaller study in a New York hospital, where the mortality rate for AIDS patients admitted with *P. aeruginosa* bacteremia was about 50% (Mendelson, M. H. et al. 1994. *Clin Infect Dis.* 18(6):886-95).

In addition, about two million Americans suffer serious burns each year, and 10,000-12,000 die from their injuries. The leading cause of death is infection (Lee, J. J. et al. (1990) *J Burn Care Rehabil.* 11(6):575-80). *P. aeruginosa* bacteremia occurs in 10% of seriously burned patients, with a mortality rate of 80% (Mayhall, C. G. (1993) p. 614-664, Prevention and control of nosocomial infections. Williams & Wilkins, Baltimore; McManus, A. T et al. (1985) *Eur J Clin Microbiol.* 4(2):219-23).

Such infections are often acquired in hospitals ("nosocomial infections") when susceptible patients come into contact with other patients, hospital staff, or equipment. In 1995 there were approximately 2 million incidents of nosocomial infections in the U.S., resulting in 88,000 deaths and an estimated cost of $ 4.5 billion (Weinstein, R. A. (1998) *Emerg Infect Dis.* 4(3):416-20). Of the AIDS patients mentioned above who died of *P. aeruginosa* bacteremia, more than half acquired these infections in hospitals (Meynard, J. L. et al. (1999) *J Infect.* 38(3):176-81).

Nosocomial infections are especially common in patients of intensive care units as these people often have weakened immune systems and are frequently on ventilators and/or catheters. Catheter-associated urinary tract infections are the most common nosocomial infection (Richards, M. J. et al. (1999) *Crit Care Med.* 27(5):887-92) (31% of the total), and *P. aeruginosa* is highly associated with biofilm growth and catheter obstruction. While the catheter is in place, these infections are difficult to eliminate (Stickler, D. J. et al. (1998) *Appl Environ Microbiol.* 64(9):3486-90). The second most frequent nosocomial infection is pneumonia, with *P. aeruginosa* the cause of infection in 21% of the reported cases (Richards, M. J. et al. (1999) *Crit Care Med.* 27(5):887-92). The annual costs for diagnosing and treating nosocomial pneumonia has been estimated at greater than $2 billion (Craven, D. E. et al. (1991) *Am J. Med.* 91(3B):44S-53S).

Treatment of these so-called nosocomial infections is complicated by the fact that bacteria encountered in hospital settings are often resistant to many antibiotics. In June 1998, the National Nosocomial Infections Surveillance (NNIS) System reported increases in resistance of *P. aeruginosa* isolates from intensive care units of 89% for quinolone resistance and 32% for imipenem resistance compared to the years 1993-1997 (NNIS. http://www.cdc.gov/ncidod/hip/NNIS/AR_Surv1198.htm). In fact, some strains of *P. aeruginosa* are resistant to over 100 antibiotics (Levy, S. (1998) *Scientific American.* March). There is a critical need to overcome the emergence of bacterial strains that are resistant to conventional antibiotics (Travis, J. (1994) *Science.* 264:360-362).

*P. aeruginosa* is also of great industrial concern (Bitton, G. (1994) Wastewater Microbiology. Wiley-Liss, New York, N.Y.; Steelhammer, J. C. et al. (1995) *Indust. Water Treatm.:* 49-55). The organism grows in an aggregated state, ie., the biofilm, which causes problems in many water processing plants. Of particular public health concern are food processing and water purification plants. Problems include corroded pipes, loss of efficiency in heat exchangers and cooling towers, plugged water injection jets leading to increased hydraulic pressure, and biological contamination of drinking water distribution systems (Bitton, G. (1994) Wastewater Microbiology. Wiley-Liss, New York, N.Y., 9). The elimination of biofilms in industrial equipment has so far been the province of biocides. Biocides, in contrast to antibiotics, are antimicrobials that do not possess high specificity for bacteria, so they are often toxic to humans as well. Biocide sales in the US run at about $ 1 billion per year (Peaff, G. (1994) *Chem. Eng. News:* 15-23).

A particularly ironic connection between industrial water contamination and public health issues is an outbreak of *P. aeruginosa* peritonitis that was traced back to contaminated poloxamer-iodine solution, a disinfectant used to treat the peritoneal catheters. *P. aeruginosa* is commonly found to contaminate distribution pipes and water filters used in plants that manufacture iodine solutions. Once the organism has matured into a biofilm, it becomes protected against the biocidal activity of the iodophor solution. Hence, a common soil organism that is harmless to the healthy population, but causes mechanical problems in industrial settings, ultimately contaminated antibacterial solutions that were used to treat the very people most susceptible to infection.

Regulation of virulence genes by quorum sensing is well documented in *P. aeruginosa*. Recently, genes not directly involved in virulence including the stationary phase sigma factor rpoS and genes coding for components of the general secretory pathway (xcp) (Jamin, M. et al. (1991) *Biochem J.* 280(Pt 2):499-506) have been reported to be positively regulated by quorum sensing. Furthermore, the las quorum sensing system is required for maturation of *P. aeruginosa* biofilms (Chapon-Herve, V. et al. (1997) *Mol. Microbiol.* 24, 1169-1170; Davies, D. G., et al. (1998) *Science* 280, 295-298). Thus it seems clear that quorum sensing represents a global gene regulation system in *P. aeruginosa*. However, the number and types of genes controlled by quorum sensing have not been identified or studied extensively.

SUMMARY OF THE INVENTION

The present invention is based, at least in part, on the discovery of a novel autoinducer molecule, 2-heptyl-3-hydroxy-4-quinolone, which functions as an intercellular signal molecule in the cell-to-cell communication system of *Pseudomonas aeruginosa*. The demonstration that 2-heptyl-3-hydroxy-4-quinolone can function as an intercellular signal sheds light on the role of secondary metabolites and shows that *P. aeruginosa* cell-to-cell signaling is not restricted to acyl-homoserine lactones.

The synthesis and bioactivity of *Pseudomonas* quinolone signal are mediated by the *P. aeruginosa* las and rhl quorum sensing systems, respectively. Accordingly, the invention is directed to bacterial quinolone signal molecules and more particularly to *Pseudomonas* quinolone signal ("PQS") molecules, e.g., 2-heptyl-3-hydroxy-4-quinolone, and analogs and derivatives thereof.

Thus, in one aspect, the invention is a compound of formula I:

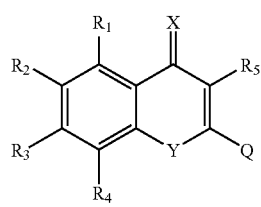

wherein:
$R_1$-$R_4$ are independently H, alkyl, alkenyl, alkynyl, OH, $NH_2$, SH, O—$R_6$, N—$R_7R_8$, or a halogen;
$R_5$ is H, SH, OH, O—$R_6$, or N—$R_7R_8$;
$R_6$ is H or $C_1$-$C_4$ alkyl;
$R_7$ and $R_8$ are independently H, $C_1$-$C_4$ alkyl, O, or S;
X and Y are independently S, O, or N—$R_9$;
$R_9$ is H, O, S, or $C_1$-$C_4$ alkyl;
Q is a tail group; and salts thereof.

In one embodiment, Q has the formula IA

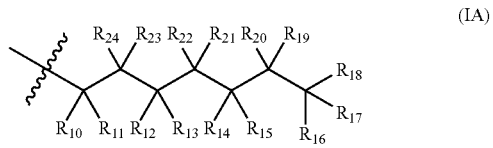

wherein:
$R_{10}$-$R_{13}$ are independently H, $C_1$-$C_4$ alkyl, OH, $NH_2$, SH, O—$R_{25}$, N—$R_{26}R_{27}$, or a halogen, or $R_{10}$ and $R_{11}$ taken together form a carbonyl, a sulfonyl or an imino moiety, or $R_{12}$ and $R_{13}$ taken together form a carbonyl, a sulfonyl or an imino moiety;
$R_{14}$-$R_{24}$ are independently H, $C_1$-$C_4$ alkyl, OH, $NH_2$, SH, O—$R_{25}$, N—$R_{26}R_{27}$, or a halogen;
$R_{25}$ is H or $C_1$-$C_4$ alkyl; and
$R_{26}$ and $R_{27}$ are independently H, $C_1$-$C_4$ alkyl, O, or S.

In certain embodiments, the invention is directed to compounds of formula I that are different than 2-heptyl-3-hydroxy-4-quinolone. Thus, examples of such embodiments include, but are not limited to, compounds of formula I in which: when Q is heptyl, X is O, Y is NH and $R_5$ is OH, $R_1$-$R_4$ are not all hydrogen; when Q is heptyl, X is O, Y is NH, and $R_1$-$R_4$ are all hydrogen, $R_5$ is not OH; when Q is heptyl, Y is NH, $R_1$-$R_4$ are all hydrogen, and $R_5$ is OH, X is not O; when Q is heptyl, X is O, $R_1$-$R_4$ are all hydrogen, and $R_5$ is OH, Y is not NH; and when X is O, Y is NH and $R_5$ is OH, and $R_1$-$R_4$ are all hydrogen, Q is not heptyl. In other embodiments, the invention is directed to compounds of formula I wherein $R_5$ is SH, OH, O—$R_6$, or N—$R_7R_8$.

In other embodiments in which Q has formula IA, $R_{16}$, $R_{17}$, and $R_{18}$ are H. In other embodiments, $R_2$ is halogen; or $R_3$ is halogen; or $R_4$ is halogen; or X is S or N—$R_9$; or Y is O, S, or N—$R_9$ and $R_9$ is $C_1$-$C_4$-alkyl; or $R_5$ is H, SH, O—$R_6$, or N—$R_7R_9$, and $R_6$ is $C_1$-$C_4$ alkyl; or $R_5$ is SH, O—$R_6$, or N—$R_7R_8$; X is O; or $R_5$ is OH and Y is N—$R_9$.

In one embodiment of invention Q is an alkylene chain having a skeleton of three to twenty carbon atoms. In certain embodiments, the alkylene chain contains one or more double bonds or triple bonds between the carbon atoms forming the skeleton alkylene side chain. In other embodiments, one or more carbon atoms forming the skeleton of the alkylene side chain are replaced with sulfur or sulfur-substituted moieties.

In yet other embodiments, the compounds of the invention contain a chiral center, for example, the Q substituent of formula IA. In certain embodiments, the compounds are optically active isomers.

In a specific embodiment, the invention is a compound of formula II:

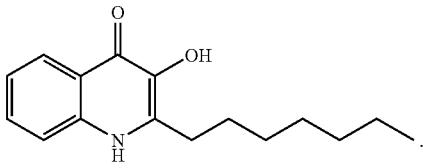

(II)

In another aspect, the invention is directed to autoinducer molecules comprising the compounds hereinabove described. In one embodiment, the autoinducer molecules regulate gene expression. In particular embodiments, the autoinducer molecule regulates gene expression in bacteria. In preferred embodiments, the bacteria is *Pseudomonas aeruginosa*. In one embodiment, the *Pseudomonas aeruginosa* gene expresses a virulence factor. In certain embodiments, the virulence factor is elastase.

In one embodiment, the autoinducer molecules of the invention regulate the activity of the LasR protein of *Pseudomonas aeruginosa*. In other embodiments, the autoinducer molecules of the invention regulate the activity of the RhlR protein of *Pseudomonas aeruginosa*. In certain embodiments, the autoinducer molecules of the invention are isolated from culture media in which *Pseudomonas aeruginosa* is grown In another embodiment, the invention is directed to compounds hereinabove defined that are capable of modulating the autoinducer activity of 2-heptyl-3-hydroxy-4-quinolone. In certain embodiments, modulation comprises inhibition of the autoinducer activity of 2-heptyl-3-hydroxy-4-quinolone. In other embodiments, modulation comprises synergistic enhancement of the autoinducer activity of 2-heptyl-3-hydroxy-4-quinolone.

In yet another embodiment, the invention is directed to compounds hereinabove described that are capable of modulating the activity of the LasR and/or the RhlR proteins of *Pseudomonas aeruginosa*. In certain embodiments, the compound is an agonist of the LasR and/or the RhlR proteins of *Pseudomonas aeruginosa*. In certain embodiments, the compound is an antagonist of the LasR and/or the RhlR proteins of *Pseudomonas aeruginosa*.

In another aspect, the invention is a pharmaceutical composition comprising a therapeutically effective amount of a compound of formula I and a pharmaceutically acceptable carrier therefor, wherein the compound inhibits the activity of one or more proteins in a microorganism that regulate expression of virulence factors. In particular embodiments of the pharmaceutical composition, the compound is present in an amount effective to affect the ability of the microorganism to initially infect or further infect an organism. In one embodiment, the microorganism is *Pseudomonas aeruginosa*. In other embodiments of the invention where the microorganism is *Pseudomonas aeruginosa*, the compound of the pharmaceutical composition inhibits the activity of the LasR and/or the RhlR proteins of *Pseudomonas aeruginosa*. In certain other embodiments, the compound of the pharmaceutical composition inhibits the autoinducer activity of 2-heptyl-3-hydroxy-4-quinolone. The pharmaceutical composition may further comprise an antimicrobial, antibacterial or antifungal agent.

In yet another aspect, the invention is a method of inhibiting the infectivity of *Pseudomonas aeruginosa* comprising administering to a subject a therapeutically effective amount of a compound of formula I, wherein the compound inhibits the activity of the LasR and/or the RhlR proteins of *Pseudomonas aeruginosa*. In certain embodiments, the compound inhibits the autoinducer activity of 2-heptyl-3-hydroxy-4-quinolone.

Another aspect of the invention is a method of treating an immunocompromised subject infected with *Pseudomonas aeruginosa* comprising administering to a subject a therapeutically effective amount of a compound of formula (I), wherein the compound inhibits the activity of the LasR and/or the RhlR proteins of *Pseudomonas aeruginosa*. In certain embodiments, the compound inhibits the autoinducer activity of 2-heptyl-3-hydroxy-4-quinolone. In particular embodiments, the subject is afflicted with cystic fibrosis.

In yet another embodiment, the invention is a culture medium for microorganisms comprising, as an added compound, an autoinducer molecule of the invention, at a concentration effective to stimulate or promote the metabolism, growth and/or recovery of the microorganism. In certain embodiments, the microorganism is *Pseudomonas aeruginosa*. In particular embodiments where the microorganism is *Pseudomonas aeruginosa*, the autoinducer is 2-heptyl-3-hydroxy-4-quinolone.

Yet another aspect of the invention is a method for identifying a compound that modulates an autoinducer molecule in bacteria, said method comprising:
providing a cell which comprises a quorum sensing controlled gene, wherein said cell is responsive to an autoinducer molecule of the invention as hereinabove described, such that a detectable signal is generated;
contacting said cell with an autoinducer as hereinabove described in the presence and absence of a test compound; and
detecting a change in the detectable signal to thereby identify said test compound as a modulator of an autoinducer molecule in bacteria. In certain embodiments, the test compound inhibits the autoinducer molecule. In other embodiments, the compound synergizes activity of the autoinducer molecule. In preferred embodiments, the bacteria is *Pseudomonas aeruginosa*. In particular embodiments of the invention when the microorganism is *Pseudomonas aeruginosa*, the autoinducer is 2-heptyl-3-hydroxy-4-quinolone. In other embodiments of the invention when the microorganism is *Pseudomonas aeruginosa*, the compound inhibits binding of the autoinducer molecule to LasR and/or RhlR.

Still another aspect of the invention is a method of regulating the expression of a gene in bacteria comprising:
inserting a gene into bacteria chosen for enhancement of gene expression by a compound of formula I that enhances the activity of the LasR and/or RhlR protein; and
incubating the bacteria with a compound of formula I that enhances the activity of the LasR protein, such that the expression of the gene is regulated. In certain embodiments, the method further comprises the additional steps of:
allowing the gene expression to reach a desired level; and
incubating the bacteria with a compound of formula I that inhibits the activity of the LasR and/or RhlR protein, thereby regulating the gene expression by the bacteria.

Another aspect of the invention is an inhibitor of the autoinducer activity of 2-heptyl-3-hydroxy-4-quinolone.

Yet another aspect of the invention is an analog of 2-heptyl-3-hydroxy-4-quinolone that inhibits the induction of virulence factors by 2-heptyl-3-hydroxy-4-quinolone, LasR or RhlR. In certain embodiments, the virulence factor is exotoxin A, elastase, or an alkaline protease.

Still another aspect of the invention is an analog of 2-heptyl-3-hydroxy-4-quinolone that inhibits the induction of biofilm formation by 2-heptyl-3-hydroxy-4-quinolone, LasR or RhlR.

In another aspect, the invention is a method for modulating quorum sensing signaling in bacteria, said method comprising:

providing bacteria that comprise a quorum sensing controlled gene, wherein said bacteria are responsive to an autoinducer molecule; and incubating the bacteria with a compound of formula I other than 2-heptyl-3-hydroxy-4-quinolone, such that quorum sensing signaling in bacteria is modulated. In one embodiment, the autoinducer is 2-heptyl-3-hydroxy-4-quinolone.

DESCRIPTION OF THE DRAWINGS

FIG. 2A includes spent culture media extracts from various *P. aeruginosa* strains added to strain PAO-R1 (lasR 2) (pTS400) and FIG. 2*b* includes culture extracts where the lasR, rhlR double mutant, strain PAO-JP3, containing pTS400 replaced strain PAO-R1.

DETAILED DESCRIPTION OF THE INVENTION

Figure 1:
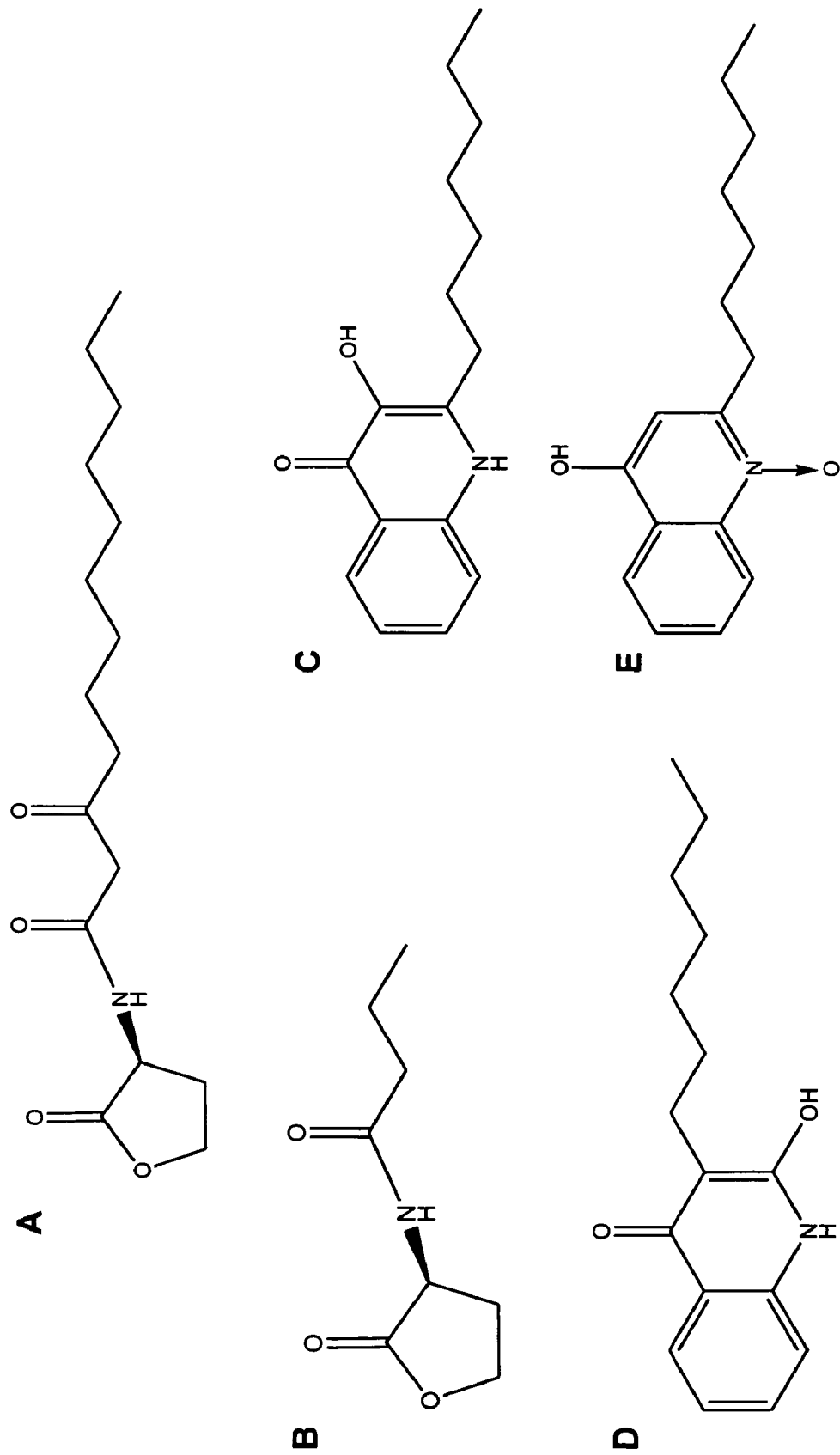
FIG. 1 is a table depicting (A) N-3-(oxododecanoyl)-L-homoserine lactone (3-oxo-C12-HSL), (B) N-butanoyl-L-homoserine lactone (C4-HSL), (C) 2-heptyl-3-hydroxy-4-quinolone, (D) 2-hydroxy-3-heptyl-4-quinolone, and (E) 2-heptyl-4-hydroxy-quinoline-N-oxide.

I. Definitions:

Before further description of the invention, certain terms employed in the specification, examples and appended claims are, for convenience, collected here.

The term "chiral" refers to molecules that have the property of non-superimposability of the mirror image partner, while the term "achiral" refers to molecules that are superimposable on their mirror image partner.

As used herein, the term "halogen" designates —F, —Cl, —Br or —I; the term "sulfhydryl" or "thiol" means —SH; the term "hydroxyl" means —OH.

The term "alkenyl" includes unsaturated aliphatic groups analogous in length and possible substitution to the alkyls described below, but which contain at least one double bond. Unless the number of carbons is otherwise specified, "lower alkenyl" refers to an alkenyl group, as defined above, but having from two to four carbon atoms in its backbone structure.

The term "alkyl" includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. The term alkyl further includes alkyl groups, which can further include heteroatoms replacing one or more carbons of the hydrocarbon backbone, e.g., oxygen, nitrogen, sulfur or phosphorous atoms. In one embodiment, a straight chain or branched chain alkyl has 20 or fewer carbon atoms in its backbone (e.g., $C_1$-$C_{12}$ for straight chain, $C_3$-$C_{12}$ for branched chain). Examples of alkyl groups contemplated by the invention include, but are not limited to, methyl, ethyl, isopropyl, isobutyl, tert-butyl, branched pentyl, branched hexyl, cyclohexyl, cyclopentyl, n-heptyl and branched heptyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), arylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl(benzyl)). Unless the number of carbons is otherwise specified, "lower alkyl" refers to an alkyl group, as defined above, but having from one to three carbon atoms in its backbone structure. The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkynyl" includes unsaturated aliphatic groups analogous in length and possible substitution to the alkyls described above, but which contain at least one triple bond. Unless the number of carbons is otherwise specified, "lower alkynyl" refers to an alkynyl group, as defined above, but having from two to four carbon atoms in its backbone structure.

The term "analog" includes compounds which are structurally similar but not identical to autoinducer molecules derived from bacteria, such as, for example, N-(3-oxododecanoyl)homoserine lactone and 2-heptyl-3-hydroxy-4-quinolone.

The term "autoinducer molecule" includes molecules that diffuse across cell membranes and activate transcription of various factors that affect bacterial viability. Such compounds can affect virulence and biofilm development. Autoinducer molecules include, for example, 2-heptyl-3-hydroxy-4-quinolone. Other examples of autoinducer molecules are listed below in Table 1. In isolated form, autoinducer molecules can be obtained from naturally occurring proteins by purifying cellular extracts, synthesized chemically, or recombinantly produced.

TABLE 1

| Bacterial species | Autoinducer Molecules for Particular Bacterial Species | Protein Modulated by Autoinducer Molecule | Target function(s) |
|---|---|---|---|
| *Vibrio fischeri* | N-3-(oxohexanoyl)-homoserine lactone (VAI-1) | LuxI/LuxR | luxICDABEG, luxR |
| | N-(octanoyl)-L-homoserine lactone (VAI-2) | AinS/AinR[c] | luminescence luxICDABEG,? |
| *Vibrio harveyi* | N-β-(hydroxybutyryl)-homoserine lactone (HAI-1) | LuxM/LuxN-LuxO-LuxR[d] | luxICDABEG, luminescence and polyhydroxybutyrate synthesis |
| | HAI-2 | Lux?/LuxPQ-LuxO/LuxR[d] | luxCDABEG |
| *Pseudomonas aeruginosa* | N-3-(oxododecanyoyl)-L-homoserine lactone (PAI-1) | LasI/LasR | lasB, lasA, aprA, toxA, virulence factors |
| | N-(butyryl)-L-homoserine lactone (PAI-2) | RhII/RhIR | rhlAB, rhamnolipid synthesis, virulence factors |
| *Pseudomonas aeureofaciens* | (PRAI) | PhzI/PhzR | phz, phenazine biosynthesis |
| *Agroacterium tumefaciens* | N-3-(oxooctanoyl)-L-homoserine lactone (AAI) | TraI/TraR-TraM | tra gens, traR, Ti plasmid conjugal transfer |
| *Erwinia carotovora subsp. carotovora* SCRI193 | VAI-1 | ExpI/ExpR | pel, pec, pep, exoenzyme synthesis |
| *Erwinia carotovora subsp. carotovora* SCC3193 | VAI-1 | CarI/CarR | cap, carbapenem antibiotic synthesis |
| *Erwinia carotovora subsp. carotovora* 71 | VAI-1 | HsII/? | pel, pec, pep, exoenzyme synthesis |
| *Erwinia stewartii* | VAI-1 | EsaI/EsaR | wts genes, exopolysaccharide synthesis, virulence factors |
| *Rhizobium leguminosarum* | N-(3R-hydroxy-7-cis-tetradecanoyl-L-homoserine lactone, small bacteriocin, (RLAI) | ?/RhiR | rhiABC, rhizosphere genes and stationary phase |
| *Enterobacter agglomerans* | VAI-1 | EagI/EagR | function unclear |
| *Yersenia enterocolitica* | VAI-1 | YenI/YenR | function unclear |
| *Serratia liquifaciens* | N-butanoyl-L-homoserine lacton (SAI-1) | SwrI? | swarming motility |
| | N-hexanoyl-L-homoserine lacton (SAI-2) | SwrI/? | swarming motility |
| *Aeromonas hydrophila* | (AHAI) | AhyI/AhyR | function unclear |
| *Escherichia coli*/?[g] | | ?/SdiA | ftsQAZ, cell division |

The term "antimicrobial" is intended to encompass the elimination or reduction of a population of microorganisms, for example, bacteria. The term is also intended to include a reduction in or elimination of the pathogenic effect of bacteria, for example through inhibition of bacterial production of virulence factors and/or biofilm development.

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings that are not aromatic so as to form a polycycle (e.g., tetralin). The term "aralkyl" includes alkyl groups substituted with at least one aryl group and aryl groups substituted with at least one alkyl group.

The term "biofilm" includes biological films that develop and persist at interfaces in aqueous and other environments. Biofilms are composed of microorganisms embedded in an organic gelatinous structure composed of one or more matrix polymers which are secreted by the resident microorganisms.

The language "biofilm development" includes the formation, growth, and modification of the bacterial colonies contained with the biofilm structures as well as the synthesis and maintenance of the exopolysaccharide matrix of the biofilm structures.

The term "biofilm associated states" includes disorders which are characterized by the presence or potential presence of a bacterial biofilm. Examples of biofilm associated states include, but are not limited to, middle ear infections, cystic fibrosis, osteomyelitis, acne, dental cavities, and prostatitis. Biofilm associated states also include infection of the subject by one or more bacteria, e.g., *Pseudomonas aeruginosa*.

The term "chain" includes moieties of atoms covalently bonded to each other linearly. Generally, the atoms in the chain may be substituted with any substituents that allow the compounds to perform their intended function. Examples of atoms which may be included in a chain of atoms include carbon, nitrogen, sulfur, oxygen, and phosphorous. For example, the linear chain may be entirely composed of carbon atoms. The carbon atoms of the chain may be substituted (e.g., with carbonyl groups, halogens, hydroxy, thiol, amino, alkyl, alkenyl, alkynyl groups etc.), unsubstituted or bound to hydrogen atoms. In addition, the carbon atoms forming the skeleton of the chain may be replaced with one or more other atoms, e.g., sulfur. Furthermore, the chain can be saturated (e.g., contain only single bounds) or may be unsaturated (e.g., contain double or triple bonds between the atoms of the chain or their substituents.)

The term "compound" includes molecules of any one of formulae, as described herein, or pharmaceutically acceptable salts, esters, or prodrugs thereof. The term "compound" includes analogs of autoinducer molecules as well as inhibitors of autoinducer molecules. Thus, the term "compound" includes antimicrobial agents, which inhibit or modulate the formation of bacterial virulence factors and/or bacterial biofilms.

The term "heteroatom" includes atoms of any element other than carbon or hydrogen. Preferred heteroatoms are nitrogen, oxygen, sulfur and phosphorus.

The language an "immunocompromised subject" includes subjects, e.g., mammals, e.g., humans, which have an immune system that is incapable of reacting to pathogens. The subject can be immunocompromised due to a genetic disorder, disease or drugs that inhibit immune response. An immunocompromised subject includes an individual afflicted with cystic fibrosis or who is taking corticosteroids or immunosuppressive agents.

The language "infected with *Pseudomonas aeruginosa*" includes a subject that is found to have *Pseudomonas aeruginosa*, present in its body. For example, *Pseudomonas aeruginosa* often infects the lungs of cystic fibrosis patients. Even a small number of *Pseudomonas aeruginosa* found in an organism can constitute infection with *Pseudomonas aeruginosa*.

The language "inhibitor of the autoinducer molecule" includes compounds of the invention and other compounds that interfere with the ability of the autoinducer molecule to stimulate, regulate, or modulate the activity of the protein which is normally responsive to it. For example, inhibitors of *P. aeruginosa* autoinducer molecules include compounds which degrade, compete with, or bind to, for example, 2-heptyl-3-hydroxy-4-quinolone, or otherwise alter the ability of the autoinducer molecule to interact with the LasR protein and/or the RhlR protein of *P. aeruginosa*.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The terms "effective amount" and "therapeutically effect amount" are used interchangeably and are intended to include the amount of a compound of the invention given or applied to an organism or subject that allows the compound to perform its intended therapeutic function. The effective amounts of the compound of the invention will vary according to factors such as the degree of infection in the subject, the age, sex, and weight of the subject, and the ability of the compound to inhibit the activity of the protein regulated by the autoinducer molecule of the bacteria upon, for example, the LasR protein of P. aeruginosa in the subject. Dosage regimes can be adjusted to provide the optimum therapeutic response. For example, several divided doses can be administered daily or the dose can be proportionally reduced as indicated by the exigencies of the therapeutic situation.

The term "subject" includes organisms which are can suffer from biofilm associated states. The term subject includes mammals, e.g., horses, monkeys, bears, dogs, cats, mice, rabbits, cattle, squirrels, rats, and, preferably, humans. In a further embodiment, the subject may be immunocompromised.

The language "synergist of the autoinducer molecule" is intended to include molecules that enhance the ability of the autoinducer molecule to stimulate the protein modulated by the autoinducer molecule (e.g., such as the LasR protein for P. aeruginosa).

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "tail group" includes groups that allow the compound of the invention to perform its intended function. In an embodiment, the tail group of the compound of the invention is hydrophobic. In another embodiment, the tail group is a chain of three to twenty atoms, such as carbon, nitrogen, sulfur, oxygen, or phosphorous. The tail group may be substituted or unsubstituted, saturated or unsaturated. In an embodiment, the tail group is unsubstituted or substituted alkyl, alkenyl, or alkynyl. In an embodiment, the tail group is substituted with one or more halogens (e.g., fluorine, chlorine, bromine or iodine). In another further embodiment, the tail group is substituted with at least one $C_1$-$C_4$ group (e.g., methyl, ethyl, isopropyl, n-propyl, t-butyl, iso-butyl, or n-butyl.) In an embodiment, the tail group is a chain of from about 5 atoms to about 15 atoms, 5 atoms to about 14 atoms, about 5 atoms to about 13 atoms, about 5 atoms to about 12 atoms, about 5 atoms to about 11 atoms, about 5 atoms to about 10 atoms, about 5 atoms to about 9 atoms, about 6 atoms to about 9 atoms, about 7 atoms to about 8 atoms, about 7 atoms, and about seven carbons. In a further embodiment, the tail group is heptyl.

The term "modulator", as in "modulator of an autoinducer molecule" is intended to encompass, in its various grammatical forms, induction and/or potentiation, as well as inhibition and/or down regulation of quorum sensing controlled gene expression. As used herein, the term "modulator of quorum sensing signaling" includes a compound or agent that is capable of modulating or regulating at least one quorum sensing controlled gene or quorum sensing controlled genetic locus, e.g., a quorum sensing controlled genetic locus in P. aeruginosa. A modulator may act to modulate signal generation (e.g., the synthesis of a quorum sensing signal molecule, i.e., autoinducer molecule), signal reception (e.g., the binding of a signal molecule to a receptor or target molecule), or signal transmission (e.g., signal transduction via effector molecules to generate an appropriate biological response). In one embodiment, a method of the present invention encompasses the modulation of the transcription of an indicator gene in response to an autoinducer molecule. In another embodiment, a method of the present invention encompasses the modulation of the transcription of an indicator gene, preferably an quorum sensing controlled indicator gene, by a test compound.

The term "quorum sensing signaling" or "quorum sensing" is intended to include the generation of a cellular signal in response to cell density. In one embodiment, quorum sensing signaling mediates the coordinated expression of specific genes. A "quorum sensing controlled gene" is any gene, the expression of which is regulated in a cell density dependent fashion. In a preferred embodiment, the expression of a quorum sensing controlled gene is modulated by a quorum sensing signal molecule, e.g., an autoinducer molecule (e.g., a quinolone molecule of the invention). The term "quorum sensing signal molecule" is intended to include a molecule that transduces a quorum sensing signal and mediates the cellular response to cell density. In a preferred embodiment the quorum sensing signal molecule is a freely diffusible autoinducer molecule, e.g., 2-heptyl-3-hydroxy-4-quinolone or analog thereof. In one embodiment, a quorum sensing controlled gene encodes a virulence factor (e.g., exotoxin A, elastase, alkaline protease). In another embodiment, a quorum sensing controlled gene encodes a protein or polypeptide that, either directly or indirectly, inhibits and/or antagonizes a bacterial host defense mechanism. In yet another embodiment, a quorum sensing controlled gene encodes a protein or polypeptide that regulates biofilm formation.

II. Methods

Quorum sensing in P. aeruginosa first was discovered because of the ability of 3-oxo-C12-HSL and LasR to induce the expression of the lasB gene, which encodes for the elastin-hydrolyzing protease, LasB (3, 5, 6, 9). Subsequently, the expression of lasB also was shown to be controlled by C4-HSL and RhlR, indicating that both known P. aeruginosa cell-to-cell signals were involved in the regulation of this major virulence factor (4, 10-12). During the analysis of C4-HSL production, it was determined that *P. aeruginosa* was capable of producing a third unknown signal that activated lasB. This observation led to the discovery and identification of a novel *P. aeruginosa* cell-to-cell signal molecule.

This novel molecule belongs to the 4-quinolone chemical family, which is best known for the antibiotic activity of many of its members. The signal has been shown to be 2-heptyl-3-hydroxy-4-quinolone and it has been designated as the *Pseudomonas* quinolone signal (PQS), shown in FIG. 1C in comparison to known autoinducers 3-oxo-C12-HSL and C4-HSL. It has also been shown that this compound induces lasB in *P. aeruginosa* and depends on the *P. aeruginosa* quorum sensing systems for its production and bioactivity.

Discovery of a Novel Cell-To-Cell Signal

The LasB elastase (also known as elastolytic protease and elastin-hydrolyzing protease) is a significant *P. aeruginosa* virulence factor that is controlled by both the las and rhl quorum sensing systems (6, 8). It has been shown that the transcription of lasB is greatly reduced in either a *P. aeruginosa* lasI or rhlI mutant, indicating the importance of 3-oxo-C12-HSL and C4-HSL, respectively (11, 12). Consistent with this finding, strain PAO-R1 (pTS400), which contains a LasR null mutation and a lasB'-lacZ fusion, does not express elastase or β-gal (6, 7). This phenotype results from the absence of LasR, which positively regulates genes controlled by the las quorum sensing system including rhlR, which is required for the rhl quorum sensing system to function (8, 20, 21). As expected, the absence of lasR also renders the lasB'-lacZ fusion in strain PAO-R1 (lasR 2) (pTS400) unresponsive to 3-oxo-C12-HSL (4). Additionally, lasB'-lacZ in this strain is mildly activated by exogenously added C4-HSL, which is most likely attributable to the presence of low amounts of RhlR that can be produced in the absence of LasR (4, 20).

Figure 2:
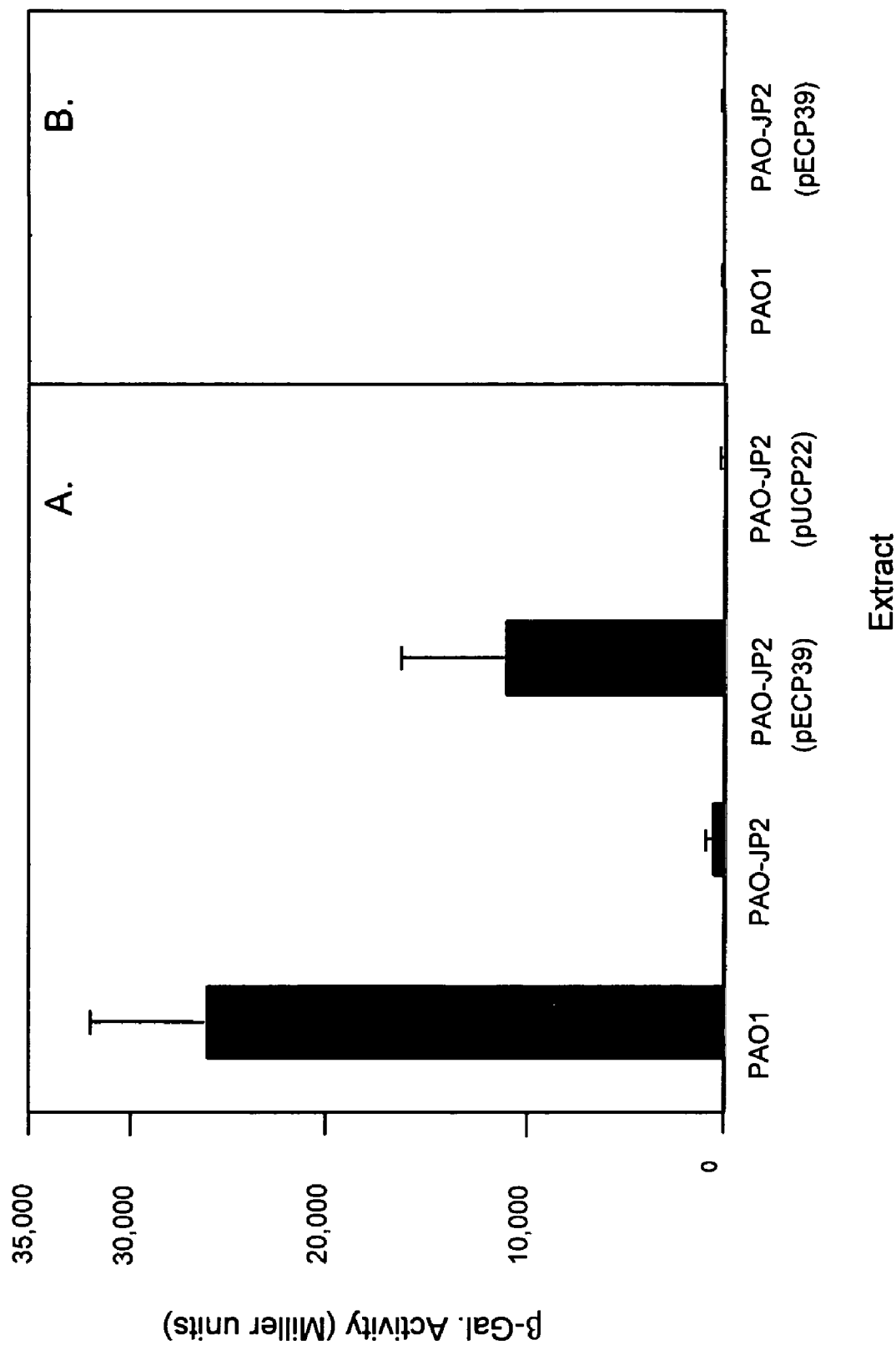
FIG. 2 is a graph depicting the induction of lasB'-lacZ fusion (as measured by the level of β-Gal. activity) of various culture extracts.

Therefore, it was surprising to find that the addition of a spent culture media extract from *P. aeruginosa* strain PAO1 (wild type) to strain PAO-R1 (lasR 2) (pTS400) caused a major induction of lasB'-lacZ (FIG. 2A). Furthermore, this induction could not be mimicked with the addition of synthetic 3-oxo-C12-HSL and/or C4-HSL, indicating that an unknown third signal was present in the media from the wild-type strain PAO1. HPLC separation of a strain PAO1 spent media extract resulted in two fractions that activated the lasB promoter in strain PAO-R1 (lasR 2) (pTS400). One fraction co-eluted with C4-HSL, and the other eluted near 3-oxo-C12-HSL. It was presumed that the material that eluted near 3-oxo-C12-HSL was a novel cell-to-cell signal.

The lack of lasB'-lacZ induction in strain PAO-R1 (lasR⁻) (pTS400) without the addition of extract (5) showed that production of the novel signal required LasR and presumably 3-oxo-C12-HSL. Thus, HPLC purification of the novel signal from wild-type strain PAO1 was hampered by the fact that it was not readily separated from 3-oxo-C12-HSL, which is required for LasR activity.

This technical difficulty was overcome by construction of a gene that encoded an autoinducer-independent form of LasR. This truncated LasR, referred to as ΔLasR, has a large N-terminal deletion and is encoded on plasmid pECP39. The ΔLasR protein, which was based on a similar truncated construct of the *Vibrio fischeri* LuxR protein (a LasR homolog) (22), can activate LasR-controlled genes in the absence of 3-oxo-C12-HSL. Therefore, ΔLasR was used to induce the production of the novel signal in strain PAO-JP2 (lasI⁻, rhlI⁻). The double autoinducer mutant, strain PAO-JP2, was transformed with plasmid pECP39, and it was found that a spent culture media extract from this strain contained the novel signal that activated lasB'-lacZ in strain PAO-R1 (lasR⁻) (pTS400) (FIG. 2A). There were no lasB'-lacZ activating signals in spent media extracts from cultures of strain PAO-JP2 (lasI⁻, rhlI⁻) alone or containing the control vector pUCP22 (FIG. 2A). This confirmed that the synthesis of the new signal depended on LasR and indicated that the signal was not produced by a known autoinducer synthase because strain PAO-JP2 did not have a functional LasI or RhlI.

An initial analysis of the novel signal activity showed that, when the lasR, rhlR double mutant, strain PAO-JP3, containing pTS400 replaced strain PAO-R1(lasR⁻) (pTS400) in our bioassay, the signal in culture extracts of strains PAO1 and PAO-JP2 (lasI⁻, rhlI⁻) (pECP39) was no longer able to induce lasB'-lacZ (FIG. 2B). This suggested that rhlR was required for the bioactivity of the new signal.

Using this information, an experiment was conducted to define the requirements for signal activity by developing an *E. coli* bioassay for the signal. *E. coli* strain DH5a was transformed with plasmid pECP62.5, which contained the lasB'-lacZ reporter and the inducible tacp-rhlR gene. If the signal worked directly through RhlR, then the induction of tacp-rhlR in the presence of exogenously added signal should result in the activation of lasB'-lacZ in *E. coli* strain DH5a (pECP62.5). It was determined that the signal did not induce lasB'-lacZ when RhlR was expressed in *E. coli* strain DH5a (pECP62.5). This suggested that the signal's requirement for rhlR may be attributable to an additional *P. aeruginosa* component that is controlled by RhlR or, alternatively, that *E. coli* may be less permeable to this signal.

Purification and Identification of the Novel Cell-To-Cell Signal

Figure 3:
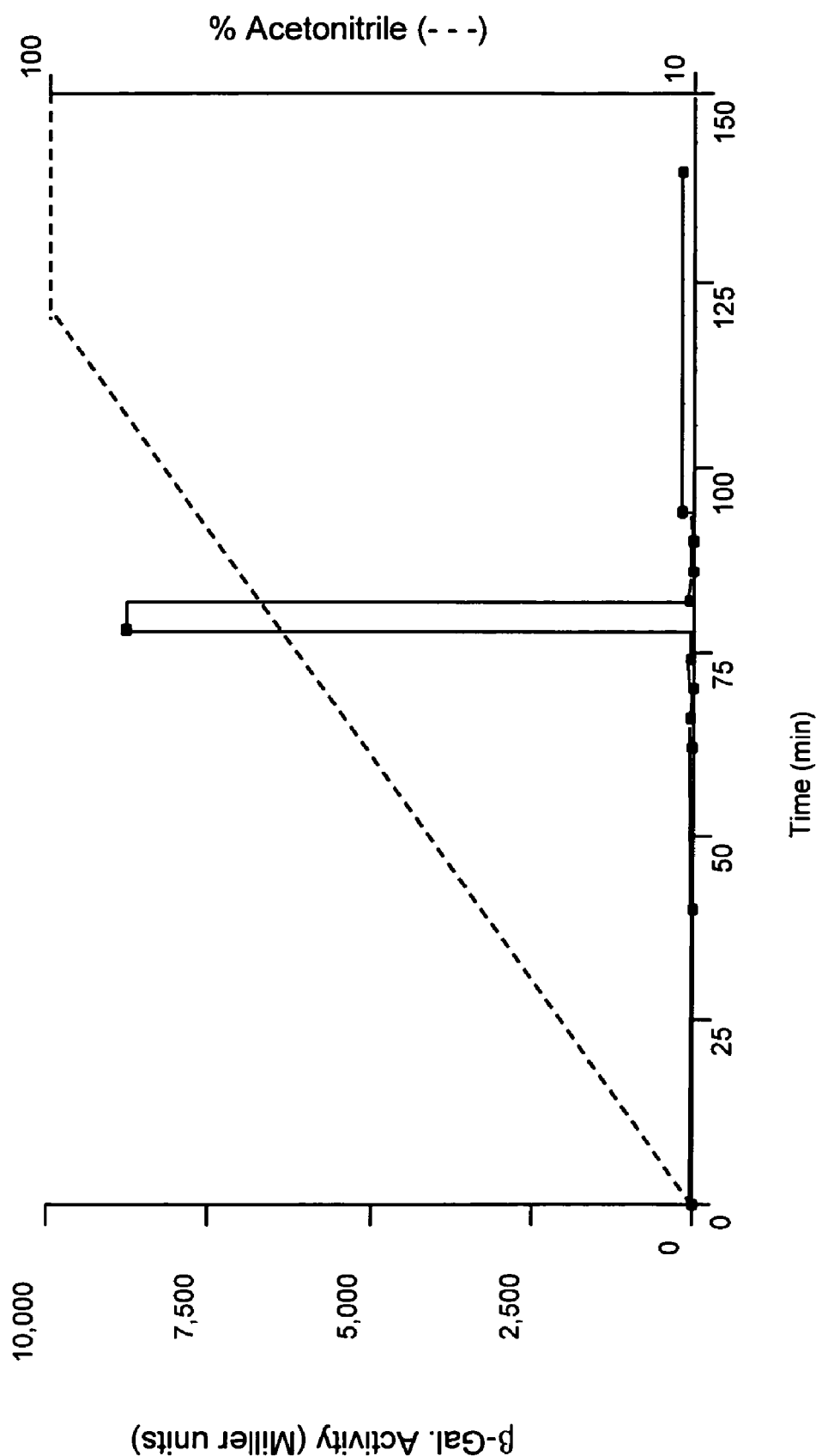
FIG. 3 is a graph depicting the HPLC analysis of a spent media extract from a culture of strain PAO-JP2 (lasI⁻, rhlI⁻) (pECP39) in an acetonitrile/water gradient.

HPLC analysis of a spent media extract from a culture of strain PAO-JP2 (lasI⁻, rhlI⁻) (pECP39) showed that a single peak of bioactivity was eluted from an acetonitrile/water gradient (FIG. 3).

This indicated that if multiple signals capable of activating lasB'-lacZ were produced, they would be similar with regard to their hydrophobicity. The eluted signal was further purified by preparative TLC and was chemically analyzed to determine its structure.

Chemical analysis of the purified signal indicated that, unlike most other Gram-negative autoinducers, it was not an acylated homoserine lactone. Low-resolution mass spectroscopy analysis showed a molecular ion of m/z 259 and a fragmentation pattern consistent with an alkylquinolone that had an additional oxygenation on the heteroaromatic core (FIG. 4A). The ultraviolet spectrum and downfield signals of the $^1$H NMR (FIG. 5A) were similar to those of the known 3-hydroxy-2-methyl-4-quinolone (23, 24). However, the molecular ion and upfield signals of the $^1$HNMR (FIG. 5A) suggested the presence of a heptyl rather than a methyl chain in position 2. High-resolution mass spectroscopy gave a molecular ion with an m/z of 259.1571, consistent with the chemical composition C16H21NO2 (calculated 5259.1572). Taken together, this data indicated that the novel signal was 2-heptyl-3-hydroxy-4-quinolone (FIG. 1C), which was designated as the *Pseudomonas* quinolone signal (PQS).

Analysis of Synthetic PQS

To confirm the identification of PQS, synthetic 2-heptyl-3-hydroxy-4-quinolone was prepared by sequential Duff reaction (25) and Dakin oxidation (26) of 2-heptylquinolone (27). The low-resolution mass spectrum (FIG. 4B), high-resolution mass spectrum (m/z of 259.1578), and $^1$H NMR spectrum (FIG. 5B) of synthetic 2-heptyl-3-hydroxy-4-quinolone were indistinguishable from those of purified natural PQS. Synthetic and natural PQS were also identical with regard to ultraviolet spectroscopy and TLC analysis. Furthermore, the synthetic material was active in the PQS bioassay.

Figure 6:
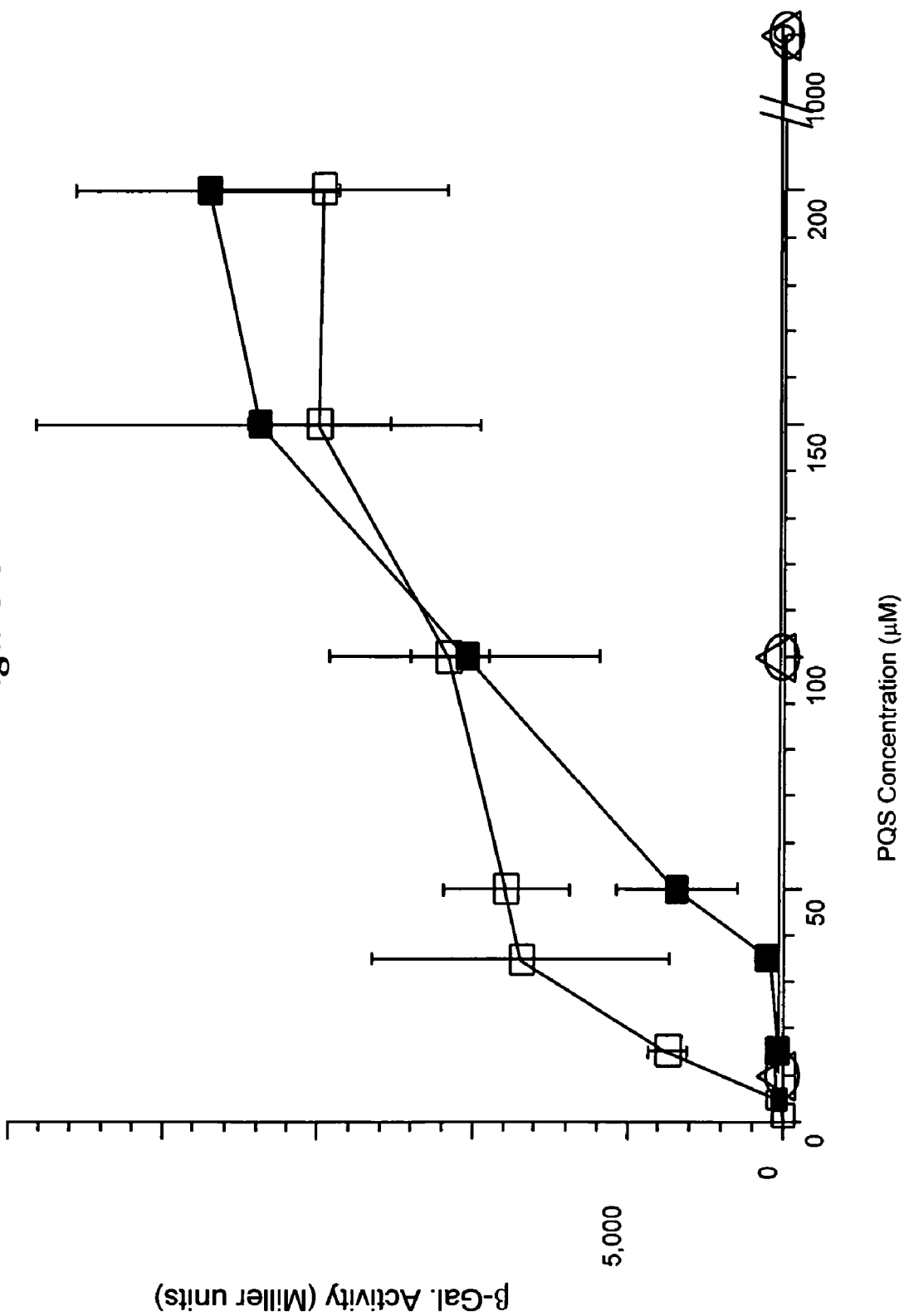
FIG. 6 is a graph depicting the induction of lasB'-lacZ in strain PAO-R1 (lasR⁻) (pTS400) in the presence of increasing concentrations of synthetic or natural PQS.

In the presence of increasing concentrations of synthetic or natural PQS, there was a dose-dependent induction of lasB'-lacZ in strain PAO-R1 (lasR⁻) (pTS400) (FIG. 6). The purification of PQS from a 1.2-liter culture of strain PAO-JP2 (lasI⁻, rhlI⁻) (pECP39) yielded an average of 1.8 mg of PQS, which is equivalent to a concentration of ≅6 mM in the culture fluid. This concentration, which is likely to be an underestimate of the actual amount in culture fluid (assuming the total recovery in the purification was 100%), was within the range required for activation of the lasB promoter in *P. aeruginosa* strain PAO-R1 (lasR⁻) (pTS400) (FIG. 6; 5 mM synthetic PQS 5 148 Miller units).

It is also interesting to note here that two PQS analogs were not capable of activating lasB'-lacZ in strain PAO-R1 (lasR⁻) (pTS400). Despite their structural similarities to PQS, the compounds 2-hydroxy-3-heptyl-4-quinolone (FIG. 1D) and 2-heptyl-4-hydroxy-quinoline-N-oxide (FIG. 1E) were not active when tested in the PQS bioassay described above (FIG. 6). These results suggested that the PQS target may be specific with regard to the compounds by which it is activated, although these two analogs were not tested in a competitive assay to determine that the analogs did not bind to the PQS target.

Discussion

The present invention demonstrates that *P. aeruginosa* produces a cell-to-cell signal that is unlike any previously reported intercellular signal molecule. This molecule was determined to have a 4-quinolone base structure and therefore has been designated as the *Pseudomonas* quinolone signal (PQS). Furthermore, exogenously added PQS induced a lasB'-lacZ fusion in the *P. aeruginosa* lasR mutant, strain PAO-R1, containing the plasmid pTS400. This indicated that there is a third cell-to-cell signal, in addition to the autoinducers 3-oxo-C12-HSL and C4-HSL, that is involved in lasB induction by *P. aeruginosa*. Despite the ability of PQS to activate lasB'-lacZ in the absence of lasR, the production of PQS required an active LasR protein. This suggested that a gene (or genes) required for PQS synthesis is controlled through the las quorum sensing system. It was also determined that at least RhlR was required for PQS to act as a signal because lasB'-lacZ was not induced by PQS in the lasR, rhlR double mutant, strain PAO-JP3, containing the plasmid pTS400.

Although the basis of the requirement for rhlR is not known, it is suggested that RhlR may serve to regulate the expression of a *P. aeruginosa* gene that is involved in the response to PQS. This suggestion is based on the fact that the PQS response was not replicated by the addition of PQS to a recombinant *E. coli* strain expressing RhlR in the presence of lasB'-lacZ. These initial experiments on PQS indicated that this signal depended on both *P. aeruginosa* quorum sensing systems and that it was involved in the regulation of the major virulence factor, LasB elastase. The addition of a third molecule to the *P. aeruginosa* intercellular signal repertoire increases the complexity of the quorum sensing hierarchy.

With regard to the relationship of these cell-to-cell signals, the data presented herein implies that 3-oxo-C12-HSL is required for the production of PQS, and previous results suggested that 3-oxo-C12-HSL also positively regulates the production of C4-HSL (20, 21). These findings further suggest that 3-oxo-C12-HSL can be considered the dominant *P. aeruginosa* cell-to-cell signal that is responsible, with LasR, for initiating the start of the quorum sensing response.

The relationship between PQS and C4-HSL is difficult to determine from the data. To act as signals, both molecules require RhlR. The C4-HSL signal has been shown to interact with RhlR (12), but it is not clear whether PQS acts directly or indirectly through RhlR. In either case, it is possible that PQS and C4-HSL produce an additive effect on the induction of lasB.

To facilitate the purification of PQS, a mutated lasR gene was constructed that encoded a truncated protein (ΔLasR) capable of activating LasR-controlled genes in the absence of 3-oxo-C12-HSL. PQS was purified by sequential reverse phase column chromatography and TLC from the double autoinducer mutant, strain PAO-JP2, that was expressing the ΔLasR protein. Based primarily on the spectral properties of the purified material, it was concluded that the novel signal molecule was 2-heptyl-3-hydroxy-4-quinolone. This compound was synthesized, and all chemical analysis (including high and low resolution MS, $^1$H NMR spectra, UV spectra, and TLC) showed that synthetic 2-heptyl-3-hydroxy-4-quinolone was identical to natural PQS. As a confirmation of the structural assignment, we showed that synthetic PQS, but not other similar quinolones, had biological activity.

Based on the activity profile of synthetic PQS and the amount of signal purified from *P. aeruginosa* culture fluid, it can be conservatively estimated that the concentration of PQS in culture fluid was ≅6 mM, which is in the active concentration range. This concentration is similar to the approximate concentrations of 3-oxo-C12-HSL (1 to 5 mM; refs. 3 and 4) and C4-HSL (10 mM; ref. 4) found in culture supernatants. The amount of PQS required to activate the bioassay to half of its maximum activity was ≅30 mM. Similar *P. aeruginosa* bioassays for 3-oxo-C12-HSL and C4-HSL showed that a concentration of ≅1 mM was required for these signals to activate their respective assays to half of their maximum activity (4). These differences suggest that, with regard to lasB'-lacZ induction, the relative potency of PQS may not be as high as the potencies of 3-oxo-C12-HSL and C4-HSL.

It has been well established that 4-quinolones are secondary metabolites that can have potent antibiotic activity (28). It is now evident that at least one member of this family of molecules, 2-heptyl-3-hydroxy-4-quinolone, has a role in cell-to-cell signaling. The modern 4-quinolone antibiotics are halogenated at the 6 or 8 position and are commonly used to treat a variety of both Gram-positive and Gram-negative infections (29). These molecules are bactericidal and are believed to target DNA gyrase, which can be naturally mutated in *P. aeruginosa* to produce resistant strains (30, 31).

Despite the development of this resistance phenotype, some 4-quinolone antibiotics have a secondary effect in resistant strains. The synthesis of a number of virulence factors, many of which (including elastase) are controlled by quorum sensing, is reduced by 4-quinolone antibiotics (32). This finding is supported by in vivo studies in which 4-quinolone antibiotic therapy has been shown to reduce lung damage in rats without decreasing the bacterial population (33). The mechanisms of such activities are unknown. However, the data presented herein indicate that 4-quinolone antibiotics may interfere with 4-quinolone signaling and gene activation, and further indicate that 4-quinolone signal molecules may be a viable target for the development of antibacterial therapies.

It is also interesting to note that many synthetic 4-quinolones are exported by active efflux (reviewed in ref. 34) and recent reports show that active efflux is involved in the export of the *P. aeruginosa* autoinducer 3-oxo-C12-HSL (35, 36). This leads to the speculation that PQS may be exported by active efflux and that this transport mechanism could be involved in multiple cell-to-cell signaling pathways. *P.*

*aeruginosa* produces a myriad of secondary metabolites, most of which (including 4-quinolones) were discovered because they possess an observable bioactivity such as antibacterial or phytotoxic activity (28).

PQS does not have detectable anti-*Staphylococcus aureus* or anti-*E. coli* activity. However, this molecule showed activity as an intercellular signal that induced the *P. aeruginosa* virulence gene lasB. These findings lead to the conclusion that although acyl-homoserine lactones represent one type of cell-to-cell signal in *P. aeruginosa*, there are also other types of intercellular signals involved in the regulation of virulence gene expression.

Furthermore, it has previously been shown that other Gram-negative bacteria produce quorum sensing signals that are not acyl-homoserine lactones. For example, *Ralstonia solanacearum* has been shown to produce a fatty acid methyl ester that acts as a signal (37), and both *E. coli* and *Salmonella typhimurium* produce an unidentified intercellular signal that appears to not be an acyl-homoserine lactone (38). The discovery that 4-quinolones can act as intercellular signals demonstrates that bacterial cell-to-cell signals are an increasingly diverse group of molecules. The elucidation of the mechanism by which PQS regulates lasB should be an important first step toward understanding the role of this type of signaling in *P. aeruginosa* virulence.

EXEMPLIFICATION

The invention is further illustrated by the following examples that should not be construed as limiting.

Strains, Plasmids, and Reagents.

The following bacterial strains were used in this study: *Escherichia coli* strain DH5a (13); the wild-type *P. aeruginosa* strain PAO1 (14); and the PAO1 mutant strains PAO-JP2 (lasI$^-$, rhlI$^-$) (12), PAO-JP3 (lasR, rhlR) (12), and PAO-R1 (lasR) (6). Unless otherwise indicated, bacterial cultures were grown in peptone trypticase soy broth (15) supplemented with 200 mg/ml carbenicillin where appropriate. Plasmid pECP39, which encodes a truncated form of LasR (ΔLasR) that is capable of activating LasR-controlled genes in the absence of an autoinducer, was constructed as follows. First, the intermediate plasmid pKDT39 was constructed by ligating the lasR DNA that encodes LasR amino acids 160-239 in-frame to the histidine fusion site of the expression vector pTRCH is C (Invitrogen). This resulted in the trcp-ΔlasR fusion, which encodes for a truncated, autoinducer-independent form of LasR, the expression of which is controlled by the trc promoter. The trcp-ΔlasR-containing DNA fragment from pKDT39 then was ligated into the *P. aeruginosa* cloning vector pUCP22 (16) to form pECP39 (bla, lacI$^q$, trcp-ΔlasR, oriP, oriC). Plasmid pTS400 (5) contains a lasB'-lacZ translational fusion, and plasmid pECP62.5 (12) contains tacp-rhlR and a lasB'-lacZ translational fusion. Trans-formations and other molecular techniques were completed with standard procedures (17). The PQS analog 2-hydroxy-3-heptyl-4-quinolone (FIG. 1D) was synthesized as described (18), and 2-heptyl-4-hydroxy-quinoline-N-oxide (FIG. 1E) was purchased from Sigma.

Example 1

The PQS Bioassay

To monitor PQS bioactivity, 1-ml cultures of *P. aeruginosa* strain PAO-R1 (pTS400) were grown for 18 h at 37° C. with shaking (260 rpm; initial optical density was 0.02 at 660 nm) in the presence of culture extract or synthetic PQS. This was followed by measuring activation of the lasB'-lacZ fusion with the use of β-galactosidase (β-gal) assays as described by Miller (19). For culture extracts, bacterial culture fluid was extracted with ethyl acetate and was prepared as described (3). Extracts that were resuspended in ethyl acetate were added to bioassay tubes, and ethyl acetate was removed by drying under a stream of nitrogen. Unless otherwise specified, the amount of material assayed was extracted from 10 ml of culture fluid.

Example 2

Thin Layer Chromatography (TLC) and High Performance Liquid Chromatography (HPLC)

Preparative TLC plates were obtained by making 1-mm layers of a slurry of 55-g silica gel G (Machery & Nagel) in a solution of 5 g of KH2PO4 in 95 ml of water on 20-×20-cm glass plates. Plates then were air-dried and activated at 100° C. for 1 h. The solvent for TLC was a 17:2:1 mixture of dichloromethane-acetonitrile-dioxane (vol/vol). HPLC was performed on a Beckman-Altex Ultra-sphere 10-mm×25-cm C18 reverse phase column. Extracts were resuspended in 0.25 ml of methanol and were loaded onto the column that then was eluted (2 ml/min) with an acetonitrile/water gradient (10-100% over 120 min). Fractions were collected at the indicated intervals and were dried by rotary evaporation at room temperature. Evaporated samples were stored at 220° C. before being dissolved in methanol and were assayed for PQS activity.

Example 3

Purification of PQS

PQS was purified from 1.2 liters of *P. aeruginosa* strain PAO-JP2 (pECP39) that was grown for 24 h at 37° C. with shaking (260 rpm; initial optical density was 0.05 at 660 nm). Cultures were centrifuged for 10 min at 10,000×g, and spent supernatant was removed and extracted twice with ethyl acetate as described (3). The ethyl acetate extract was dried with sodium sulfate and was concentrated by rotary evaporation at room temperature. The concentrated material then was extracted and concentrated three times with progressively smaller volumes of a 1:1 mixture of ethyl acetate and acetonitrile (final volume, 0.75 ml). This concentrated extract was fractionated by using Short Body C18 Sep-Pak Plus cartridges (Waters). After loading the extract onto a cartridge (0.25 ml per cartridge), it was washed with 10, 30, and 40% acetonitrile in water (3 ml per cartridge). The active material then was eluted with 55% acetonitrile in water. This partially purified extract was dissolved in 0.3 ml of 90% dioxane in water and was further purified by preparative TLC. After loading the extract, the TLC plate was eluted twice with 17:2:1 dichloromethaneyacetonitrileydioxane. A fluorescent blue band ex-tending from Rƒ0.30-0.48 was removed and eluted with 1:1 acetonitrile/ethyl acetate (3×3 ml). The eluate, which contained 2-heptyl-3-hydroxy-4-quinolone (FIG. 1C), was concentrated and analyzed as described below.

Example 4

Chemical Analysis of Natural and Synthetic PQS $^1$H and $^{13}$C NMR spectra in DMSO-d6 were recorded on a Bruker (Billerica, Mass.) AM400 NMR spectrometer operating at 400 MHz for 1H or 100.5 MHz for $^{13}$C. The chemical shifts are reported in δ (ppm) relative to residual DMSO-d5 (2.49 ppm) for $^1$H or relative to DMSO-d6 (39.43 ppm) for $^{13}$C, and coupling constants are given in hertz. Infrared (IR) spectra were recorded on a Perkin-Elmer 1600 series Fourier Transformed-IR. Melting points were recorded on a Mel-Temp melting point apparatus and are uncorrected. The ultraviolet spectra were recorded on a Shimadzu UV-1601 PC spectrophotometer. Low-resolution MS were recorded on a Hewlett-Packard 5973 mass selective detector fitted with an SIS direct insertion probe, and high-resolution electron impact spectra were recorded at the University of California-Riverside Mass Spectrometry Facility.

Example 5

Synthesis of PQS

A mixture of 2-heptylquinolone (2.00 g, 8.22 mmol), hexamine (0.58 g, 4.11 mmol), and trifluoroacetic acid (12.3 ml) was stirred at reflux under argon for 27 h. Methanol (20 ml) and water (20 ml) were added, and heating was continued for 50 min. Hydrochloric acid (2.5 M, 10 ml) was added, and heating was continued for 30 min. The mixture was allowed to cool, and the precipitate was removed by filtration and was washed with water. The solid was triturated with acetone (10 ml) and then was removed by filtration to give 3-formyl-2-heptylquinolone (0.99 g, 44%), which crystallized from methanol/ethyl acetate as colorless needles: mp 244-247° C. (dec) (Found: C, 75.55; H, 7.95; N, 5.09%. C17H21NO2 requires C, 75.24; H, 7.80; N, 5.16%). $^1$H NMR 12.11 (br s, 1H), 10.37 (s, 1H), 8.12 (d, J 8.0, 1H), 7.70 (dd, J 8.2, 7.1, 1H), 7.57 (d, J 8.2, 1H), 7.38 (dd, J 8.0, 7.1, 1H), 3.01 (t, J 7.7, 2H), 1.56 (quin., J 7.4, 2H), 1.39-1.16 (m, 8H), 0.82 (t, J 6.4, 3H). $^{13}$C NMR 190.7 (d), 178.0 (s), 159.9 (s), 139.1 (s), 132.9 (d), 126.1 (s), 124.8 (d), 124.9 (d), 118.6 (d), 113.3 (s), 31.5 (t), 31.1 (t), 28.9 (t), 28.8 (t), 28.3 (t), 22.0 (t), 13.8 (q). m/z 271 (5%), 253 (8%), 242 (5%), 228 (3%), 214 (8%), 200 (13%), 187 (20%), 172 (16%), 159 (100%), 130 (8%).

Figure 4:
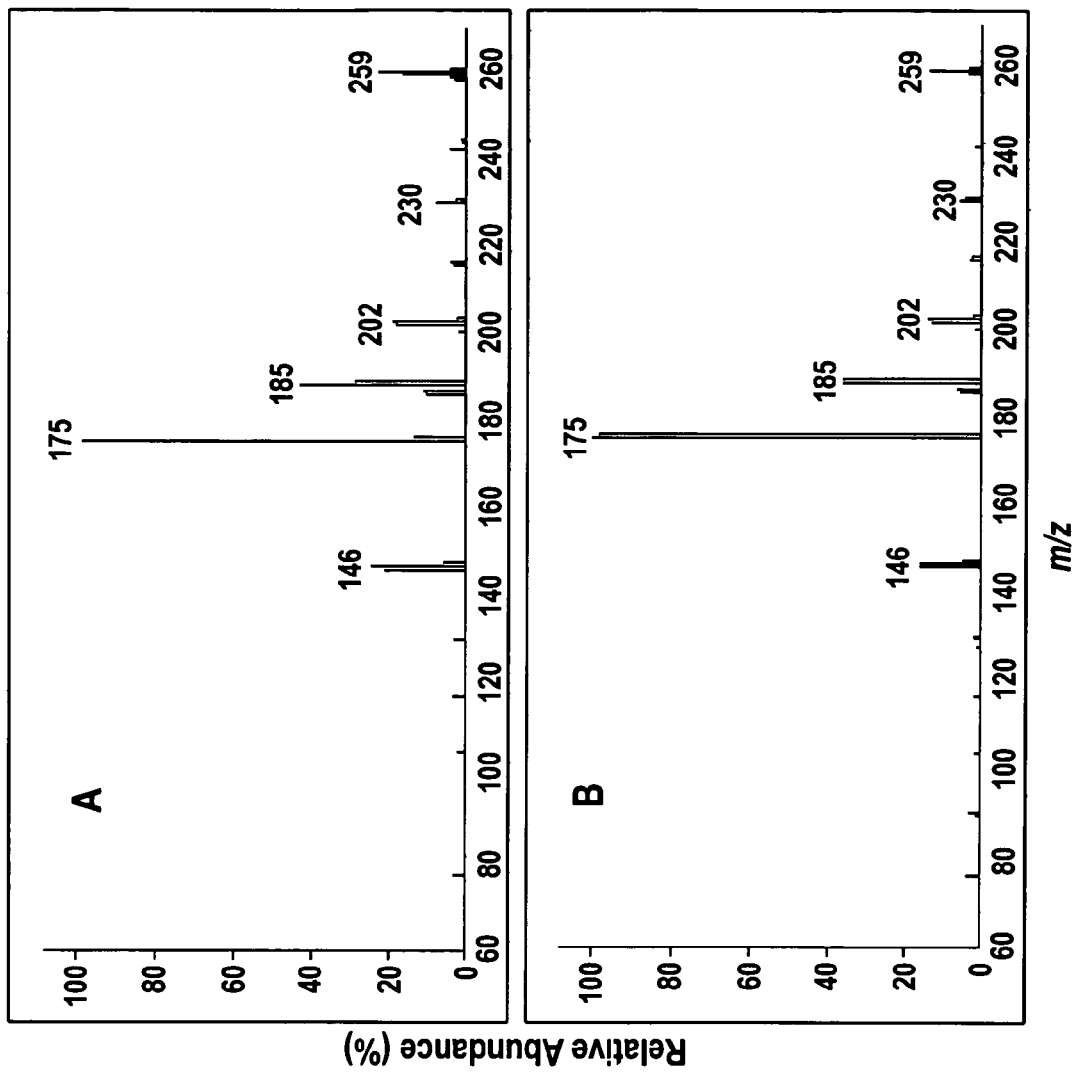
FIG. 4 is a graph depicting low-resolution mass spectroscopy analysis of (4A) the purified signal shown in FIG. 3 and (4B) synthetic 2-heptyl-3-hydroxy-4-quinolone.
Figure 5:
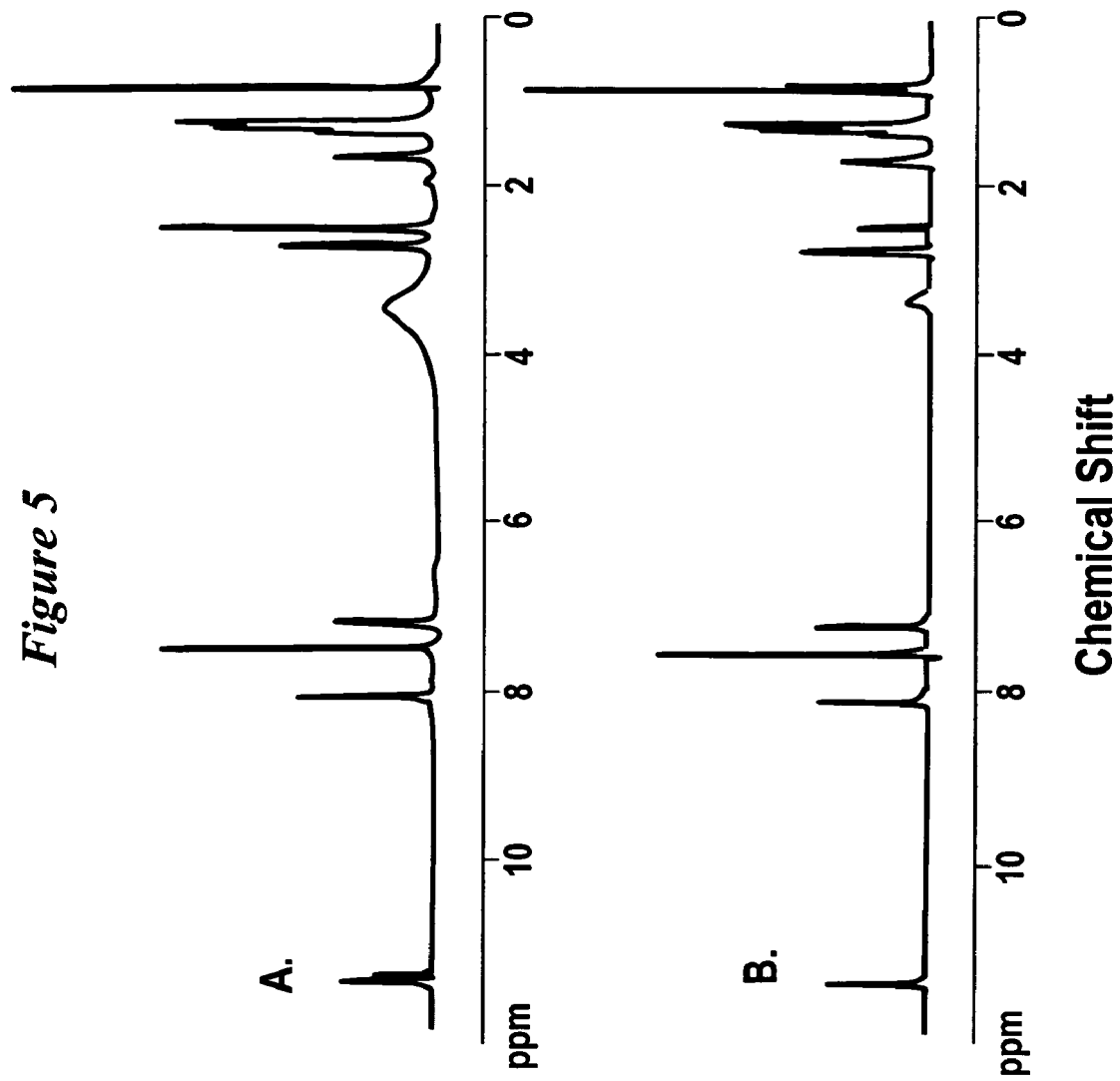
FIG. 5 is a graph depicting $^1$H NMR analysis of (5A) the purified signal shown in FIG. 3 and (5B) synthetic 2-heptyl-3-hydroxy-4-quinolone.

Aqueous hydrogen peroxide (1.05 M, 1.49 ml, 1.56 mmol) was added to a solution of 3-formyl-2-heptylquinolone (0.41 g, 1.49 mmol) in ethanol (4.5 ml) and aqueous sodium hydroxide (1.08 M, 1.49 ml, 1.6 mmol) under argon, and the mixture was stirred at room temperature for 6 h. The precipitate was removed by filtration, was air dried, and was crystallized from ethyl acetate to give 2-heptyl-3-hydroxy-4-quinolone (0.29 g, 74%), as off-white needles: mp 196-198° C. (dec) (Found: C, 74.30; H, 8.42; N, 5.21%. C16H21NO2 requires C, 74.10; H, 8.16; N, 5.40%). λmax (log ε) methanol 217 (4.43), 250 (4.56), 292 (3.34), 343 (4.08), 351 nm (4.08). $v_{max}$ (KBr) 3,275, 2,929, 1,639, 1,599, 1,558, 1,488, 1,467, 1,416, 1,367, 1,265, 1,115, 1,073, 1,025, 954, 934, 863, 756, 710, 895, 574 cm$^{-1}$. $^{13}$C NMR 168.8 (s), 137.7 (s), 137.3 (s), 135.4 (s), 129.8 (d), 124.4 (d), 122.1 (s), 121.4 (d), 117.7 (d), 31.1 (t), 28.7 (t), 28.4 (t), 28.0 (t), 27.7 (t), 21.9 (t), 13.8 (q). $^1$H NMR and Mass Spectrometry data of synthetic PQS are shown in FIGS. 4 and 5.

LIST OF REFERENCES

1. Fuqua, W. C., Winans, S. C. & Greenberg, E. P. (1996) *Annu. Rev. Microbiol.* 50, 727-751.
2. Pesci, E. C. & Iglewski, B. H. (1999) in *Cell-Cell Signaling in Bacteria*, eds. Dunny, G. & Winans, S. C. (Am. Soc. Microbiol., Washington, D.C.), pp. 147-155.
3. Pearson, J. P., Gray, K. M., Passador, L., Tucker, K. D., Eberhard, A., Iglewski, B. H. & Greenberg, E. P. (1994) *Proc. Natl. Acad. Sci. USA* 91, 197-201.
4. Pearson, J. P., Passador, L., Iglewski, B. H. & Greenberg, E. P. (1995) *Proc. Natl. Acad. Sci. USA* 92, 1490-1494.
5. Passador, L., Cook, J. M., Gambello, M. J., Rust, L. & Iglewski, B. H. (1993) *Science* 260, 1127-1130.
6. Gambello, M. J. & Iglewski, B. H. (1991) *J. Bacteriol.* 173, 3000-3009.
7. Parsek, M. R., Schaefer, A. L., Greenberg, E. P. (1997) *Mol. Microbiol.* 26, 301-310.
8. Ochsner, U. A., Koch, A. K., Fiechter, A. & Reiser, J. (1994) *J. Bacteriol.* 176, 2044-2054.
9. Morihara, K. (1964) *J. Bacteriol.* 88, 745-757.
10. Winson, M. K., Camara, M., Latifi, A., Foglino, M., Chhabra, S. R., Daykin, M., Bally, M., Chapon, V., Salmond, G. P. C., Bycroft, B. W., et al. (1995) *Proc. Natl. Acad. Sci. USA* 92, 9427-9431.
11. Brint, J. M. & Ohman, D. E. (1995) *J. Bacteriol.* 177, 7155-7163.
12. Pearson, J. P., Pesci, E. C. & Iglewski, B. H. (1997) *J. Bacteriol.* 179, 5756-5767.
13. Woodcock, D. M., Crowther, P. J., Doherty, J., Jefferson, S., DeCruz, E., Noyer-Weidner, M., Smith, S. S., Michael, M. Z. & Graham, M. W. (1989) *Nucleic Acids Res.* 17, 3469-3478.
14. Holloway, B. W., Krishnapillai, V. & Morgan, A. F. (1979) *Microbiol. Rev.* 43, 73-102.
15. Ohman, D. E., Cryz, S. J. & Iglewski, B. H. (1980) *J. Bacteriol.* 142, 836-842.
16. West, S. E., Schweizer, H. P., Dall, C., Sample, A. K. & Runyen-Janecky, L. J. (1994) *Gene* 148, 81-86.
17. Maniatis, T., Fritsch, E. F. & Sambrook, J. (1982) *Molecular Cloning: A Laboratory Manual* (Cold Spring Harbor Lab. Press, Plainview, N.Y.).
18. Laschober, R. & Stadlbauer, W. (1990) *Liebigs Ann. Chem.* 1083-1086.
19. Miller, J. A. (1972) in *Experiments in Molecular Genetics* (Cold Spring Harbor Lab. Press, Plainview, N.Y.), pp. 352-355.
20. Pesci, E. C., Pearson, J. P., Seed, P. S. & Iglewski, B. H. (1997) *J. Bacteriol.* 179, 3127-3132.
21. Latifi, A., Foglino, M., Tanaka, K., Williams, P. & Lazdunski, A. (1996) *Mol. Microbiol.* 21, 1137-1146.
22. Stevens, A. M., Dolan, K. M. & Greenberg, E. P. (1994) *Proc. Natl. Acad. Sci. USA* 91, 12619-12623.
23. Behrman, E. J., Kiser, R. L. Garas, W. F., Behrman, E. C. & Pitt, B. M. (1995) *J. Chem. Res.* M 1051-1063.
24. Spence, T. W. M. & Tennant, G. (1971) *J. Chem. Soc. C*, 3712-3719.
25. Smith, W. E. (1972) *J. Org. Chem.* 37, 3973-3974.
26. Morgan, L. R., Jr., Schunior, R. J. & Boyer, J. H. (1963) *J. Org. Chem.* 28, 260-261.
27. Somanathan, R. & Smith, K. M. (1981) *J Heterocyclic Chem.* 18, 1077-1079.
28. Leisinger, T. & Margraff, R. (1979) *Microbiol. Rev.* 43, 422-442.
29. Smith, J. T. & Zeiler, H.-J. (1998) in *Quinolone Antibacterials*, eds. Kuhlmann, J., Dalhoff, A. & Zeiler, H.-J. (Springer, Berlin), pp. 1-11.
30. Maxwell, A. & Critchlow, S. E. (1998) in *Quinolone Antibacterials*, eds. Kuhlmann, J., Dalhoff, A. & Zeiler, H.-J. (Springer, Berlin), pp. 119-166.
31. Piddock, L. V. J. (1995) *Drugs* 49, Suppl. 2, 29-35.
32. Grimwood, K., To, M., Rabin, H. R. & Woods, D. E. (1989) *Antimicrob. Agents Chemother.* 33, 41-47.
33. Grimwood, K., To, M., Rabin, H. R. & Woods, D. E. (1989) *J. Antimicrob. Chemother.* 24, 937-945.
34. Nikaido, H. (1996) *J. Bacteriol.* 178, 5853-5859.

35. Evans, K. L., Passador, L., Srikumar, R., Tsang, E., Nezezon, J. & Poole, K. (1998) *J. Bacteriol.* 180, 5443-5447.
36. Pearson, J. P., Van Delden, C. & Iglewski, B. H. (1999) *J. Bacteriol.* 181, 1203-1210.
37. Flavier, A. B., Clough, S. J., Schell, M. A. & Denny, T. P. (1997) *Mol. Microbiol.* 26, 251-259.
38. Surrette, M. G., Miller, M. B. & Bassler, B. L. (1999) *Proc. Natl. Acad. Sci. USA* 96, 1639-1644.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:
1. A compound of formula I

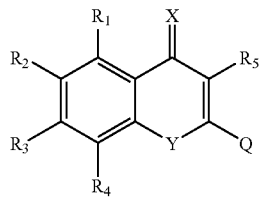

wherein:
  $R_1$-$R_4$ are independently H, alkyl, alkenyl, alkynyl, OH, $NH_2$, SH, O—$R_6$, N—$R_7R_8$, -or a halogen;
  $R_5$ is SH, OH, O—$R_6$, or N—$R_7R_8$;
  $R_6$ is H or $C_1$-$C_4$ alkyl;
  $R_7$ and $R_8$ are independently H or $C_1$-$C_4$ alkyl;
  X is S, O, or N—$R_9$;
  Y is N—$R_9$;
  $R_9$ is H or $C_1$-$C_4$ alkyl;
  Q has formula IA

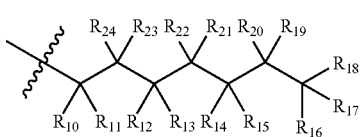

wherein:
  $R_{10}$-$R_{13}$ are independently H, $C_1$-$C_4$ alkyl, OH, $NH_2$, SH, O—$R_{25}$, N—$R_{26}R_{27}$, or a halogen, or $R_{10}$ and $R_{11}$ taken together form a carbonyl, a sulfonyl or an imino moiety, or $R_{12}$ and $R_{13}$ taken together form a carbonyl, a sulfonyl or an imino moiety;
  $R_{14}$-$R_{24}$ are independently H, $C_1$-$C_4$ alkyl, OH, $NH_2$, SH, O—$R_{25}$, N—$R_{26}R_{27}$, or a halogen;
  $R_{25}$ is H or $C_1$-$C_4$ alkyl; and
  $R_{26}$ and $R_{27}$ are independently H, $C_1$-$C_4$ alkyl, O, or S; and salts thereof.

2. The compound of claim 1 that is different than 2-heptyl-3-hydroxy-4-quinolone.
3. The compound of claim 1, wherein $R_{16}$, $R_{17}$, and $R_{18}$ are H.
4. The compound of claim 1, wherein $R_2$ is halogen.
5. The compound of claim 1, wherein $R_3$ is halogen.
6. The compound of claim 1, wherein $R_4$ is halogen.
7. The compound of claim 1, wherein X is S or N—$R_9$.
8. The compound of claim 1, wherein $R_9$ is $C_2$-$C_4$-alkyl.
9. The compound of claim 1, wherein $R_5$ is H, SH, O—$R_6$, or N—$R_7R_8$, and wherein $R_6$ is $C_1$-$C_4$ alkyl.
10. The compound of claim 1, wherein $R_5$ is SH, O—$R_6$, or N—$R_7R_8$.
11. The compound of claim 1, wherein X is O.
12. The compound of claim 11, wherein $R_5$ is OH.
13. The compound of claim 1, wherein Q is an alkylene chain having a skeleton of three to twenty carbon atoms.
14. The compound of claim 13, wherein the alkylene chain contains one or more double bonds or triple bonds between the carbon atoms forming the skeleton alkylene side chain.
15. The compound of claim 13, wherein one or more carbon atoms forming the skeleton of the alkylene side chain are replaced with sulfur or sulfur-substituted moieties.
16. The compound of claim 1, wherein the compound contains a chiral center.
17. The compound of claim 1, which is an optically active isomer.
18. A compound comprising the formula:

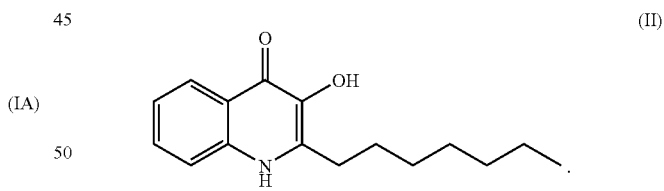

* * * * *